United States Patent
Watanabe et al.

(10) Patent No.: US 7,686,764 B2
(45) Date of Patent: Mar. 30, 2010

(54) ULTRASOUND DIAGNOSTIC APPARATUS FOR CALCULATING POSITIONS TO DETERMINE IMT AND LUMEN BOUNDARIES

(75) Inventors: Yoshinobu Watanabe, Yokohama (JP); Yoshinao Tannaka, Aiko-gun (JP); Takao Suzuki, Yokohama (JP); Hisashi Hagiwara, Yokohama (JP); Kazuhiro Sunagawa, Sendai (JP)

(73) Assignee: Panasonic Corporation, Osaka (JP)

( * ) Notice: Subject to any disclaimer, the term of this patent is extended or adjusted under 35 U.S.C. 154(b) by 720 days.

(21) Appl. No.: 10/562,319

(22) PCT Filed: Jun. 24, 2004

(86) PCT No.: PCT/JP2004/009260

§ 371 (c)(1),
(2), (4) Date: Dec. 23, 2005

(87) PCT Pub. No.: WO2004/112568

PCT Pub. Date: Dec. 29, 2004

(65) Prior Publication Data

US 2007/0123777 A1    May 31, 2007

(30) Foreign Application Priority Data

Jun. 25, 2003  (JP) ................................ 2003-181696
Jun. 30, 2003  (JP) ................................ 2003-188245

(51) Int. Cl.
 *A61B 8/00*  (2006.01)
(52) U.S. Cl. ............................................ 600/443
(58) Field of Classification Search ............ 600/454, 600/465, 437, 443
See application file for complete search history.

(56) References Cited

U.S. PATENT DOCUMENTS 5,289,821 A * 3/1994 Swartz ................... 600/455

(Continued)

FOREIGN PATENT DOCUMENTS

JP          2889568      11/1999
JP       2000-271117    10/2000

OTHER PUBLICATIONS

Hasegawa, H. et al., "Detection of lumen-intima interface of posterior wall for measurement of elasticity of the human carotid artery," Ultrasonics, Ferroelectrics and Frequency Control, IEEE Transactions on , vol. 51, No. 1, pp. 93-108, Jan. 2004.*

(Continued)

*Primary Examiner*—Eric F Winakur
*Assistant Examiner*—Helene Bor
(74) *Attorney, Agent, or Firm*—Hamre, Schumann, Mueller & Larson, P.C.

(57) ABSTRACT

An ultrasonic diagnostic apparatus includes a transmission unit that transmits at least one ultrasonic pulse from a surface of a skin of a subject toward a blood vessel (21) thereof, a reception unit (3) that receives an ultrasonic echo reflected by the blood vessel and converts the same into an electric signal to obtain a signal of the ultrasonic echo along a depth direction from the surface of the skin, a movement detection unit (5) that analyzes a phase of the ultrasonic echo signal in a direction traversing the blood vessel so as to calculate a movement amount in each of a plurality of parts included in a blood vessel wall constituting the blood vessel and a vicinity of the blood vessel wall, and a boundary detection unit (7) that detects a boundary position between the blood vessel wall and a blood flow region (22) in a lumen of the blood vessel through which blood flows based on a variation in the calculated movement amount in each part. Instability occurring when a brightness signal in image data is used can be eliminated, so that a state of a blood vessel, such as an IMT value, can be measured correctly using ultrasonic waves.

20 Claims, 17 Drawing Sheets

U.S. PATENT DOCUMENTS

| | | | |
|---|---|---|---|
| 5,628,322 A * | 5/1997 | Mine | 600/453 |
| 6,132,373 A * | 10/2000 | Ito et al. | 600/437 |
| 6,450,959 B1 * | 9/2002 | Mo et al. | 600/441 |
| 6,817,982 B2 * | 11/2004 | Fritz et al. | 600/443 |
| 6,835,177 B2 * | 12/2004 | Fritz et al. | 600/443 |
| 6,918,876 B1 * | 7/2005 | Kamiyama | 600/447 |
| 6,979,294 B1 * | 12/2005 | Selzer et al. | 600/450 |
| 7,074,187 B2 * | 7/2006 | Selzer et al. | 600/440 |
| 7,175,597 B2 * | 2/2007 | Vince et al. | 600/443 |
| 2002/0013530 A1 * | 1/2002 | Cespedes et al. | 600/454 |
| 2002/0042574 A1 * | 4/2002 | Manor et al. | 600/454 |
| 2002/0045828 A1 * | 4/2002 | Skidmore | 600/454 |
| 2002/0151795 A1 * | 10/2002 | Palti | 600/454 |
| 2003/0114756 A1 * | 6/2003 | Li | 600/437 |
| 2003/0199762 A1 * | 10/2003 | Fritz et al. | 600/437 |
| 2003/0229284 A1 * | 12/2003 | Stein | 600/454 |
| 2004/0019278 A1 * | 1/2004 | Abend | 600/454 |
| 2004/0116808 A1 * | 6/2004 | Fritz et al. | 600/437 |
| 2004/0116812 A1 * | 6/2004 | Selzer et al. | 600/467 |
| 2004/0116813 A1 * | 6/2004 | Selzer et al. | 600/467 |
| 2007/0038084 A1 * | 2/2007 | Burla et al. | 600/437 |

OTHER PUBLICATIONS

Hasegawa et al. Modified Phased Tracking Method for Measurement of Change in Thickness of Arterial Wall. Japanese Journal of Applied Physics. vol. 41 (2002) pp. 3563-3561. Part 1, No. 5B, May 2002.*

Hasegawa et al., "*Automatic Detection of Lumen-Intima Boundary of Posterior Wall of Carotid Artery*", Technical report of IEICE, US 2003-16 (Jun. 2003), pp. 5-10.

Umezawa et al., "*Measurement of Local Pulse Wave Velocity for Evaluation of Viscoelasticity from Small Vibrations on Artery Measured Using Ultrasound*", Technical report of IEICE, EA 99-42(Aug. 1999)m pp. 17-23.

* cited by examiner

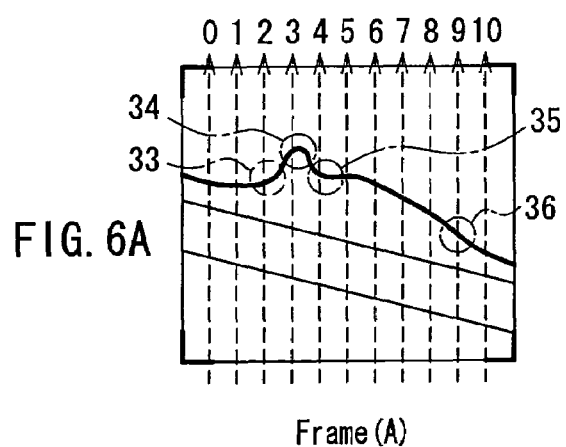
FIG. 6A Frame (A)
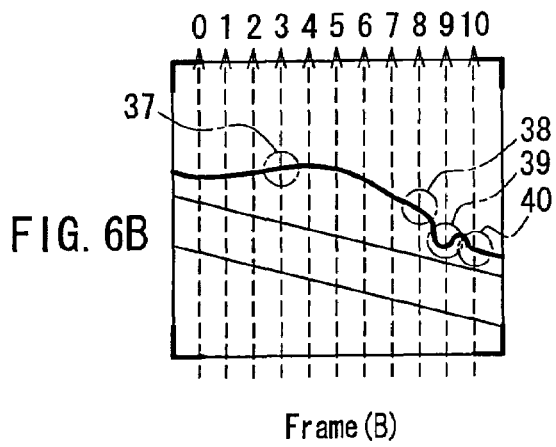
FIG. 6B Frame (B)
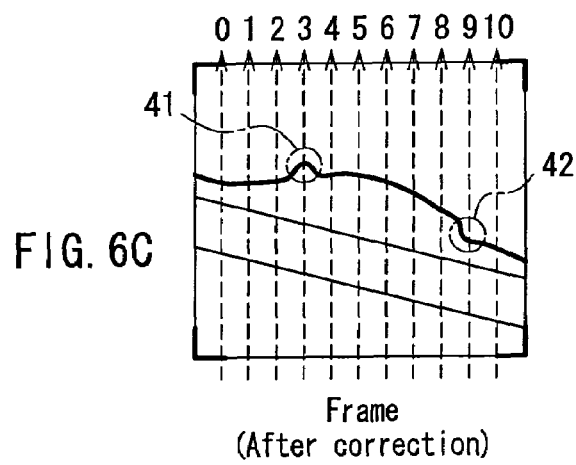
FIG. 6C Frame (After correction)

ULTRASOUND DIAGNOSTIC APPARATUS FOR CALCULATING POSITIONS TO DETERMINE IMT AND LUMEN BOUNDARIES

TECHNICAL FIELD

The present invention relates to an ultrasonic diagnostic apparatus that has a function of diagnosing a state of blood vessels using ultrasonic waves.

BACKGROUND ART

JP 2000-271117 A discloses a method of detecting a boundary of a blood vessel wall using ultrasonic waves. According to this method, assuming that a blood vessel has a normal structure, a displacement and a diameter of the blood vessel, a thickness of a blood vessel wall and the like can be measured based on a maximum peak value and a second peak value of a brightness signal in image data obtained based on ultrasonic waves reflected by the blood vessel.

Further, Japanese Patent No. 2889568 describes a method of detecting an IMT (Intima-Media Thickness: a thickness from an inner membrane to a middle membrane) value of a blood vessel wall (carotid artery) using ultrasonic waves. According to this method, assuming that a blood vessel has a normal structure, an IMT value of a blood vessel wall (carotid artery) is measured based on a maximum peak value and a second peak value of a brightness signal in image data obtained based on ultrasonic waves reflected by the blood vessel.

In the above-described conventional technologies, however, since the brightness signal of image data is utilized for analyzing a structure of the blood vessel wall as a target of the measurement, if a brightness of an inner membrane of the blood vessel wall as the target of the measurement is low, there is a problem that the displacement and the diameter of the blood vessel, the thickness of the blood vessel wall and the like cannot be measured correctly. In addition, they are based on the assumption that the structure of the blood vessel wall as the target of the measurement has a normal structure. Therefore, there is a problem that the displacement of the blood vessel or the like cannot be measured correctly if there is a local disease such as an atheroma in a blood vessel as a target of the measurement.

Similarly, in the above-described conventional technologies, the brightness signal of image data is utilized for analyzing a structure of the blood vessel wall as a target of the measurement of an IMT value. Therefore, there is a problem that the IMT value of the blood vessel wall cannot be measured correctly if a brightness of an inner membrane of the blood vessel wall as the target of the measurement is low.

DISCLOSURE OF INVENTION

It is an object of the present invention to provide an ultrasonic diagnostic apparatus that is capable of measuring a state of a blood vessel correctly using ultrasonic waves.

An ultrasonic diagnostic apparatus according to the present invention includes: a transmission unit that transmits at least one ultrasonic pulse from a skin surface of a subject toward a blood vessel thereof; a reception unit that receives an ultrasonic echo reflected by the blood vessel and converts the same into an electric signal to obtain a signal of the ultrasonic echo along a depth direction from the skin surface; a movement detection unit that analyzes a phase of the ultrasonic echo signal in a direction traversing the blood vessel so as to calculate a movement amount in each of a plurality of parts included in a blood vessel wall constituting the blood vessel and a vicinity of the blood vessel wall; and a boundary detection unit that detects a boundary position between the blood vessel wall and a blood flow region in a lumen of the blood vessel through which blood flows based on a variation in the calculated movement amount in each part.

With this configuration, the boundary position between the blood vessel wall and the blood flow region is detected based on a variation in movement amount of the blood vessel wall along the depth direction from the skin surface. Thus, the boundary position can be detected accurately without the influence of a variation in brightness value of an inner membrane existing in the subject even in the case where there is a local disease such as an atheroma in the blood vessel.

Preferably, the above configuration further includes a ROI (Region of Interest) placement unit that sets placement of a ROI where the boundary position along the depth direction from the skin surface is to be detected by the boundary detection unit. The ROI placement unit may place the ROI so as to lie over at least one of an anterior wall of the blood vessel wall on a side closer to the transmission unit and a posterior wall of the blood vessel wall on a side farther from the transmission unit.

Preferably, the transmission unit transmits a plurality of ultrasonic pulses toward a plurality of parts along a longitudinal direction of the blood vessel, and the boundary position detection unit detects the boundary position for each of the plurality of parts along the longitudinal direction of the blood vessel. With this configuration, a thickness distribution can be obtained along the longitudinal direction of the blood vessel.

Preferably, the above configuration further includes a filter processing unit that performs filter processing of data representing the boundary position along the longitudinal direction of the blood vessel that is detected by the boundary position detection unit. With this configuration, the influence of noise mixing into boundary detection of the blood vessel wall can be minimized.

Preferably, the above configuration further includes a display unit that displays an image of the blood vessel in cross section along the longitudinal direction of the blood vessel based on the boundary position along the longitudinal direction of the blood vessel that is detected by the boundary position detection unit. With this configuration, a cross section along the longitudinal direction of the blood vessel can be recognized visually.

Preferably, the above configuration further includes an average processing unit that performs average processing of data representing the boundary position that is detected by the boundary position detection unit based on data representing a boundary position obtained a predetermined number or more of measurement cycles before. With this configuration, the stability of the measurement of detecting the boundary position can be determined.

Preferably, the predetermined cycle includes a heartbeat cycle of a blood flow that flows through the blood vessel. With this configuration, a range including an allowable error range added to a movement track in the immediately preceding cycle can be compared with a movement track in the subsequent measurement cycle in synchronization with the heartbeat cycle.

Preferably, the above configuration further includes an average processing unit that performs average processing of data representing the movement amount of the blood vessel wall that is detected by the movement detection unit based on data representing a movement amount obtained a predetermined number or more of measurement cycles before. With this configuration, the stability of the measurement of detecting the movement amount of the blood vessel wall can be determined.

Another ultrasonic diagnostic apparatus according to the present invention includes: a transmission unit that transmits at least one ultrasonic pulse from a skin surface of a subject toward a blood vessel thereof; a reception unit that receives an ultrasonic echo reflected by the blood vessel and converts the same into an electric signal to obtain a signal of the ultrasonic echo along a depth direction from the skin surface; a movement detection unit that analyzes a phase of the ultrasonic echo signal in a direction traversing the blood vessel so as to calculate a movement amount in each of a plurality of parts included in a blood vessel wall constituting the blood vessel and a vicinity of the blood vessel wall; and a boundary detection unit that detects a boundary position between an inner membrane of the blood vessel and a blood flow region in a lumen of the blood vessel through which blood flows and a position of a middle membrane of the blood vessel based on a variation in the calculated movement amount in each part.

With this configuration, the boundary position between the blood vessel wall and the blood flow region and the position of the middle membrane can be detected correctly without the influence of a variation in brightness value of an inner membrane existing in the subject even in the case where there is a local disease such as an atheroma in the blood vessel.

Preferably, the above configuration further includes a ROI placement unit that sets placement of a ROI where the boundary position between the inner membrane of the blood vessel and the blood flow region and the position of the middle membrane are to be detected along the depth direction from the skin surface by the boundary detection unit. The ROI placement unit may place the ROI so as to lie over at least one of an anterior wall of the blood vessel wall on a side closer to the transmission unit and a posterior wall of the blood vessel wall on a side farther from the transmission unit. With this configuration, the boundary position of the inner membrane of the blood vessel and the blood flow region and the position of the middle membrane can be detected.

Preferably, the above configuration further includes a calculation unit that measures a thickness from the inner membrane to the middle membrane based on the boundary position and the position of the middle membrane. With this configuration, the boundary position of the inner membrane of the blood vessel and the blood flow region and the position of the middle membrane can be detected.

Preferably, the calculation unit measures the thickness from the inner membrane to the middle membrane based on a variation over time in the boundary position and a variation over time in the position of the middle membrane in one heartbeat cycle. With this configuration, the thickness from the inner membrane to the middle membrane can be measured accurately.

Preferably, the calculation unit calculates at least one of a maximum value, a minimum value and an average value of the thickness in one heartbeat cycle. With this configuration, the thickness from the inner membrane to the middle membrane can be measured by a simple method.

Preferably, the transmission unit transmits a plurality of the ultrasonic pulses toward a plurality of parts along a longitudinal direction of the blood vessel, and the calculation unit measures the thickness at each of the plurality of parts. With this configuration, a thickness distribution can be obtained along the longitudinal direction of the blood vessel.

Preferably, the above configuration further includes a display unit that displays a part where a maximum thickness is measured among the thicknesses measured at the plurality of parts. With this configuration, a thickness distribution along the longitudinal direction of the blood vessel easily can be recognized visually.

Preferably, the above configuration further includes an angle correction unit that performs angle correction with respect to a value of the thickness corresponding to an angle formed between a measuring direction of the thickness calculated by the calculation unit and a direction perpendicular to the blood vessel wall. With this configuration, a thickness of a blood vessel extending in a direction tilted with respect to the skin surface can be measured accurately.

Preferably, the above configuration further includes a stability determination unit that determines the stability of the thickness calculated by the calculation unit by comparing the thickness calculated by the calculation unit with a thickness obtained a predetermined number or more of cycles before. With this configuration, a measurer may be notified of the thus determined stability, whereby the measuring time can be shortened.

Preferably, in the above configuration, the transmission unit transmits a plurality of the ultrasonic pulses toward a plurality of parts along a longitudinal direction of the blood vessel, the calculation unit measures the thickness at each of the plurality of parts, and the ultrasonic diagnostic apparatus further includes a stability determination unit that determines stability of the thickness calculated by the calculation unit by comparing the thicknesses measured at the plurality of parts one another. With this configuration, a measurer may be notified of the thus determined stability, whereby the measuring time can be shortened.

Preferably, the above configuration further includes a unit that displays a value of the thickness calculated by the calculation unit on a monitor. With this configuration, the calculated thickness value can be visually recognized.

Preferably, the above configuration further includes a unit that displays the boundary position and the position of the middle membrane detected by the boundary detection unit on a monitor. With this configuration, the boundary position with the blood flow region and the position of the middle membrane can be recognized visually.

BRIEF DESCRIPTION OF DRAWINGS

FIGS. 6A to 6C are cross-sectional schematic views for explaining an operation of the ultrasonic diagnostic apparatus according to Embodiment 3 of the present invention.

DESCRIPTION OF THE INVENTION

The following describes embodiments of the present invention, with reference to the drawings.

Embodiment 1

Figure 1:
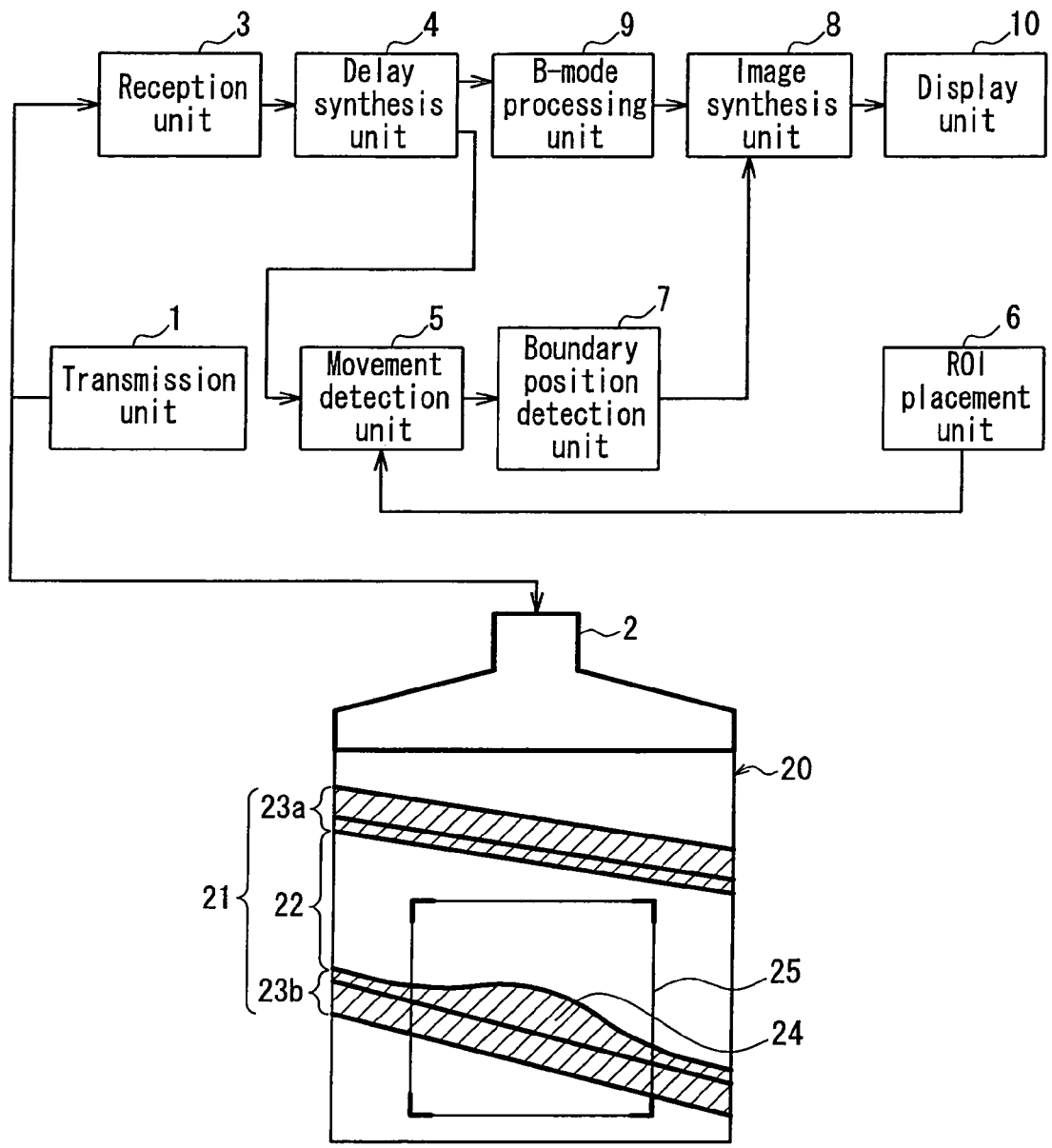
FIG. 1 is a block diagram showing a configuration of an ultrasonic diagnostic apparatus according to Embodiment 1 of the present invention.

FIG. 1 is a block diagram schematically showing a configuration of an ultrasonic diagnostic apparatus according to Embodiment 1 of the present invention. In FIG. 1, a B-mode image 20 received by this ultrasonic diagnostic apparatus also is shown. A transmission unit 1 generates an ultrasonic pulse and supplies it to an ultrasonic probe 2. The ultrasonic probe 2 transmits the ultrasonic pulse supplied from the transmission unit 1 from the skin surface of a living body toward the inside thereof. The B-mode image 20 is an image obtained when the ultrasonic pulse is transmitted toward a blood vessel 21.

In this image, the blood vessel 21 extends in a direction tilted with respect to the skin surface and is shown by an anterior wall 23a and a posterior wall 23b that define a blood flow region 22 that is the lumen through which blood flows. The anterior wall 23a is a blood vessel wall on a side closer to the ultrasonic probe 2, and the posterior wall 23b is a blood vessel wall on a side farther from the ultrasonic probe 2. In this example, the blood vessel 21 has an atheroma 24 as a local lesion that develops on an inner surface of the posterior wall 23b.

An ultrasonic echo reflected by the blood vessel 21 is converted into an electric signal by the ultrasonic probe 2, and the obtained ultrasonic echo signal is imparted to a movement detection unit 5 via a reception unit 3 and a delay synthesis unit 4. The movement detection unit 5 detects a movement amount in the respective parts along a depth direction from the surface of the skin based on the received ultrasonic echo signal. The detection of a movement amount in each region by the movement detection unit 5 can be carried out by a well-known method based on a phase change of the ultrasonic echo signal, and therefore its specific description will be omitted.

A ROI placement unit 6 sets the placement of a ROI (Region of Interest) 25 in a tomographic image, in which a boundary position along the depth direction from the skin surface is to be detected. The set ROI 25 is supplied to the movement detection unit 5. For the purpose of the present embodiment, the ROI 25 is set so as to lie over at least one of the anterior wall 23a and the posterior wall 23b.

The movement amount detected by the movement detection unit 5 is supplied to a boundary position detection unit 7. The boundary position detection unit 7 segments the interior of the ROI 25 in units of 50 μm, for example, and analyzes a state of movement (track) of each segmented parts in each heartbeat as described below, thus detecting a boundary position between the posterior wall 23b as a blood vessel wall constituting the blood vessel 21 and the blood flow region 22 in which blood flows through the blood vessel 21. The boundary position detection unit 7 further generates a two-dimensionally mapped color display image showing a cross section of the blood vessel 21, and supplies it to an image synthesis unit 8.

The ultrasonic echo signal that has passed through the reception unit 3 and the delay synthesis unit 4 is imparted also to a B-mode processing unit 9. The B-mode processing unit 9 generates image information representing a cross section of the blood vessel 21 based on the ultrasonic echo signal, and supplies it to the image synthesis unit 8. The image synthesis unit 8 synthesizes the image information supplied from the B-mode processing unit 9 and the image information supplied from the boundary position detection unit 7, and displays the resultant on a monitor of a display unit 10.

Figure 2:
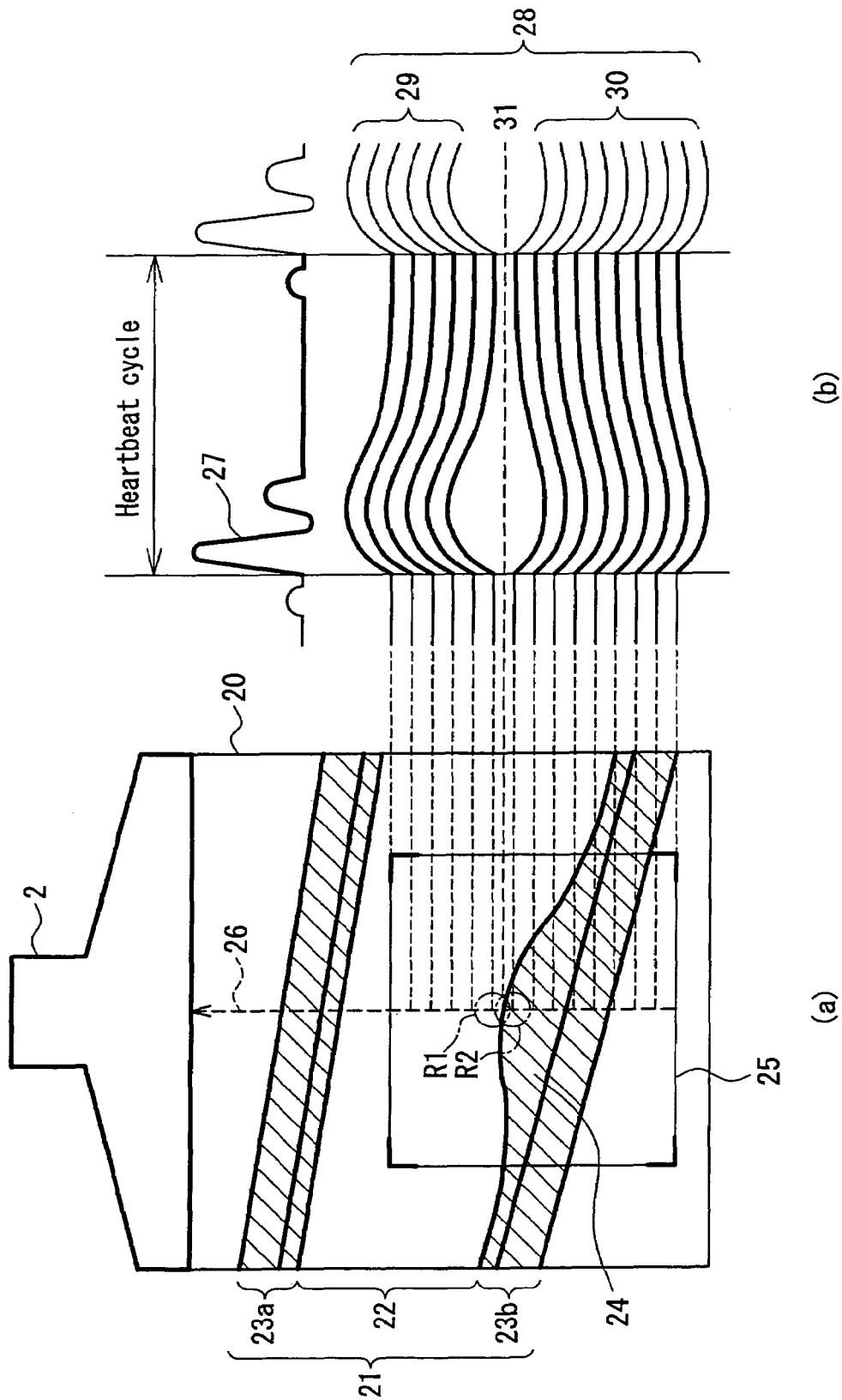
FIG. 2 is a schematic view for explaining an operation of the ultrasonic diagnostic apparatus of FIG. 1.

FIG. 2 is a schematic view for explaining an operation of the ultrasonic diagnostic apparatus according to the present embodiment. In FIG. 2, Portion (a) shows an image that is the same as the B-mode image 20 shown in FIG. 1. Portion (b) in FIG. 2 shows time-varying waveforms 28, each representing a movement amount in the depth direction from the skin surface during a heartbeat cycle based on an electrocardiograph (ECG) waveform 27. The time-varying waveforms 28 are shown for the respective parts in the ROI 25 within a scanning line 26 of the received echo shown in Portion (a). Reference numeral 29 denotes a variation over time in the respective parts of the blood flow region 22, and reference numeral 30 denotes a variation over time in the parts in a region of the posterior wall 23b. Reference numeral 31 denotes a boundary position. By analyzing the moving state of the respective parts (track) during one heartbeat in this way, the boundary position between the blood flow region 22 through which blood flows and the region of the posterior wall 23b can be detected as follows.

In Portion (a) of FIG. 2, attention is given to point R1, and point R2 on the scanning line 26 that shows the course of the ultrasonic pulse. Point R1 is placed in the blood flow region 22 dose to the boundary position between the blood flow region 22 and the region of the posterior wall 23b. Point R2 is placed in the atheroma 24 on the posterior wall 23b dose to the boundary position.

The moving state of the respective tissues at point R1, point R2 and their peripheral parts in the ROI 25 is detected as in the waveforms 28 representing a variation in movement amount shown in Portion (b) of FIG. 2. As is evident from the drawing, the waveform 29 in the blood flow region 22 and the waveforms 30 in the region in the posterior wall 23b have tracks with different features such that their moving directions are opposite to each other. Thus, the boundary position 31 can be determined by analyzing this. In the present embodiment, for example, the midpoint of the opposite tracks can be determined as the boundary position 31.

As stated above, a variation in movement amount of a blood vessel wall in the ROI 25 is detected, and the thus obtained detected result is analyzed, whereby a boundary position between a blood flow region and a blood vessel region can be detected accurately and securely.

Further, when a variation in movement amount of the respective parts in the blood vessel wall in the ROI 25 is detected, and a difference in movement amount (thickness variation) between neighboring parts is analyzed from the thus obtained detection result, a large thickness variation will be obtained in a soft region, while a small thickness variation will be obtained in a hard region. Thus, based on this, the hardness values of the respective parts also can be detected. A boundary position between a blood flow region and a blood vessel region can be detected based on hardness values of the respective parts as in the following embodiment.

Embodiment 2

Figure 3:
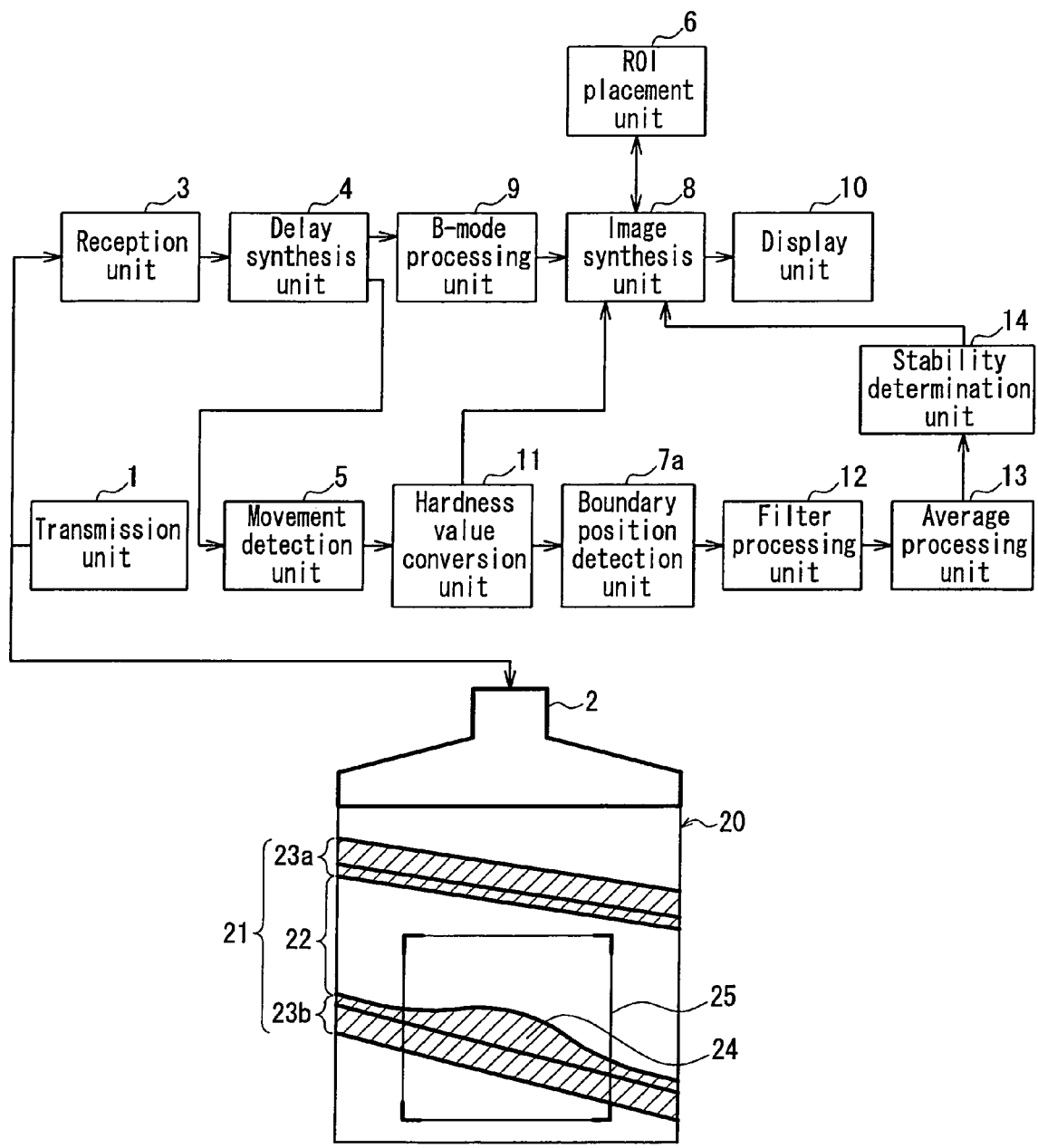
FIG. 3 is a block diagram showing a configuration of an ultrasonic diagnostic apparatus according to Embodiment 2 of the present invention.

FIG. 3 is a block diagram schematically showing a configuration of an ultrasonic diagnostic apparatus according to Embodiment 2 of the present invention. The same reference numerals are assigned to elements common to those of the ultrasonic diagnostic apparatus according to Embodiment 1 shown in FIG. 1 so as to omit the duplication of explanations.

In the present embodiment, a hardness value conversion unit 11 is provided to which an output of the detection by a movement detection unit 5 is supplied. The hardness value conversion unit 11 converts the movement amounts detected by the movement detection unit 5 into a hardness value distribution of tissues along the depth direction from the surface of the skin. An output of the hardness value conversion unit 11 is supplied to a boundary position detection unit 7a.

The boundary position detection unit 7a detects, based on the hardness value distribution of tissues along the depth direction, a boundary position between an anterior wall 23a or a posterior wall 23b as a blood vessel wall and a blood flow region 22. The boundary position detection unit 7a further generates a two-dimensionally mapped color display image showing a cross section of a blood vessel 21, and supplies it to an image synthesis unit 8. Herein, FIG. 3 illustrates a filter processing unit 12, an average processing unit 13 and a stability determination unit 14 intervening between the boundary position detection unit 7a and the image synthesis unit 8. They are illustrated for explaining the embodiment described later, and in the present embodiment the output from the boundary position detection unit 7a may be supplied directly to the image synthesis unit 8.

The image synthesis unit 8 synthesizes image information supplied from a B-mode processing unit 9 and image information supplied from the boundary position detection unit 7a, and displays the resultant on a monitor of a display unit 10.

Figure 4:
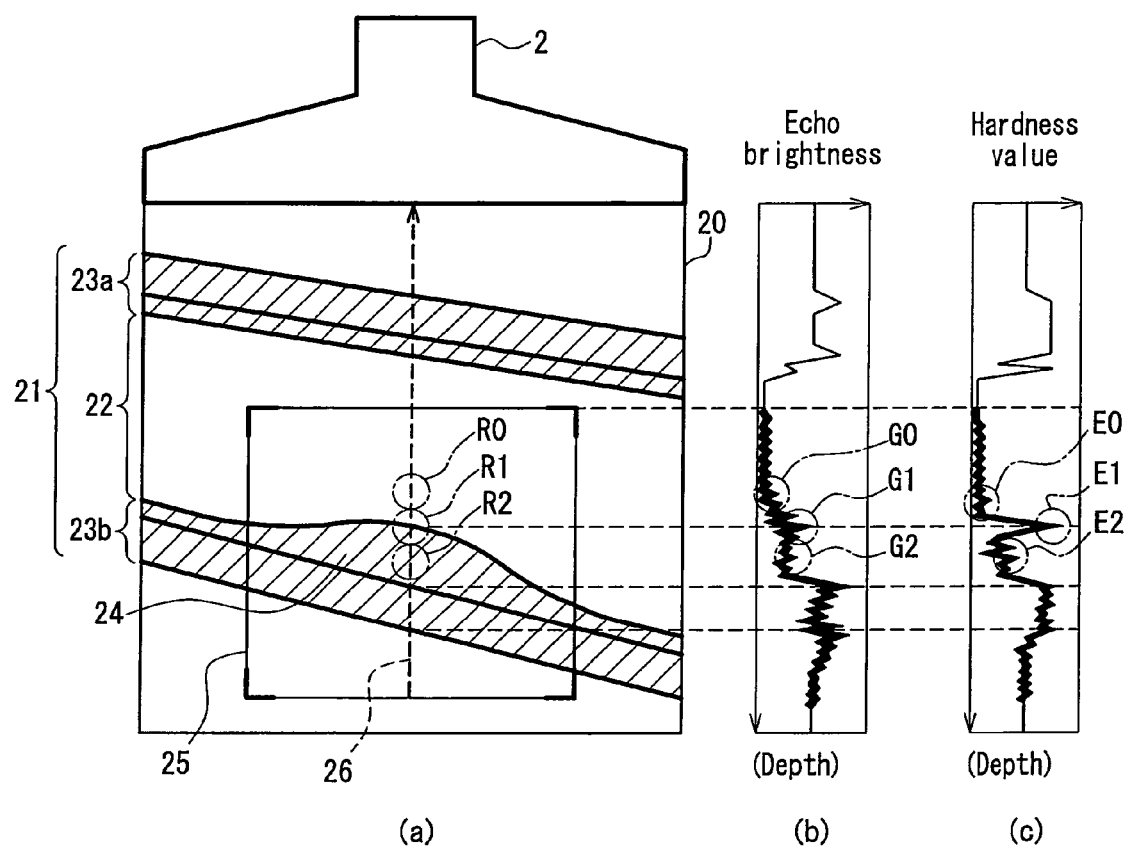
FIG. 4 is a schematic view for explaining an operation of the ultrasonic diagnostic apparatus of FIG. 3.

FIG. 4 is a schematic view for explaining an operation of the ultrasonic diagnostic apparatus according to the present embodiment. Portion (a) of FIG. 4 shows an image that is the same as the B-mode image 20 shown in FIG. 3. Portions (b) and (c) in FIG. 4 show waveforms. Portion (b) shows the case where echo brightness, detected based on an ultrasonic echo signal obtained by receiving an ultrasonic echo reflected by the blood vessel 21, is utilized for detecting a boundary position of the posterior wall 23b and the blood flow region 22. Portion (c) shows the case where a boundary position is detected by utilizing hardness values of tissues that are converted by the hardness value conversion unit 11.

Attention is given to point R0, point R1 and point R2 on a scanning line 26 that shows the course of an ultrasonic pulse. Point R0 is placed in the blood flow region 22, point R1 is placed at a boundary position between the posterior wall 23b and the blood flow region 22, and point R2 is placed in an atheroma 24 on the posterior wall 23b.

As shown by the waveform in Portion (b) of FIG. 4 that shows a relationship between the echo brightness and the depth from the surface of the skin, the echo brightness has a property of varying gently from point G0 corresponding to the blood flow region 22 to point G2 corresponding to the inside of the atheroma 24 via point G1 corresponding to the boundary position between the posterior wall 23b and the blood flow region 22. Further, depending on the compositions of contents making up the atheroma 24, unevenness of the echo brightness may occur. For that reason, when point G1 corresponding to the boundary position is to be detected, there is a strong possibility that error occurs in the direction from point G1 to point G0 or the direction from G1 to point G2. Thus, when the measurement of a blood vessel with the atheroma 24 is attempted, which requires detailed diagnosis, it is difficult to detect the boundary position between the blood vessel wall and the blood flow region accurately.

In contrast, the use of hardness values of tissues converted by the hardness value conversion unit 11 as in the present embodiment allows point E1, corresponding to point R1 placed at the boundary position between the posterior wall 23b and the blood flow region 22, to show a much higher peak value than those of point E0 corresponding to R0 placed in the blood flow region 22 and point E2 corresponding to point R2 placed in the atheroma 24, which is free from the influence of the echo brightness as shown in the waveform of Portion (c) of FIG. 4. Thus, the boundary position between the blood vessel wall and the blood flow region can be detected accurately and securely.

As stated above, according to the present embodiment, the boundary position detection unit 7a detects, based on the distribution of hardness values of tissues along the depth direction from the surface of the skin, point R1 indicating the boundary position between the blood vessel wall constituting the blood vessel 21 and the blood flow region. Therefore, the boundary position between the blood vessel wall and the blood flow region can be detected correctly without the influence of a variation in brightness value of an inner membrane existing in the subject even in the case where there is a local lesion such as an atheroma in the blood vessel.

Figure 5:
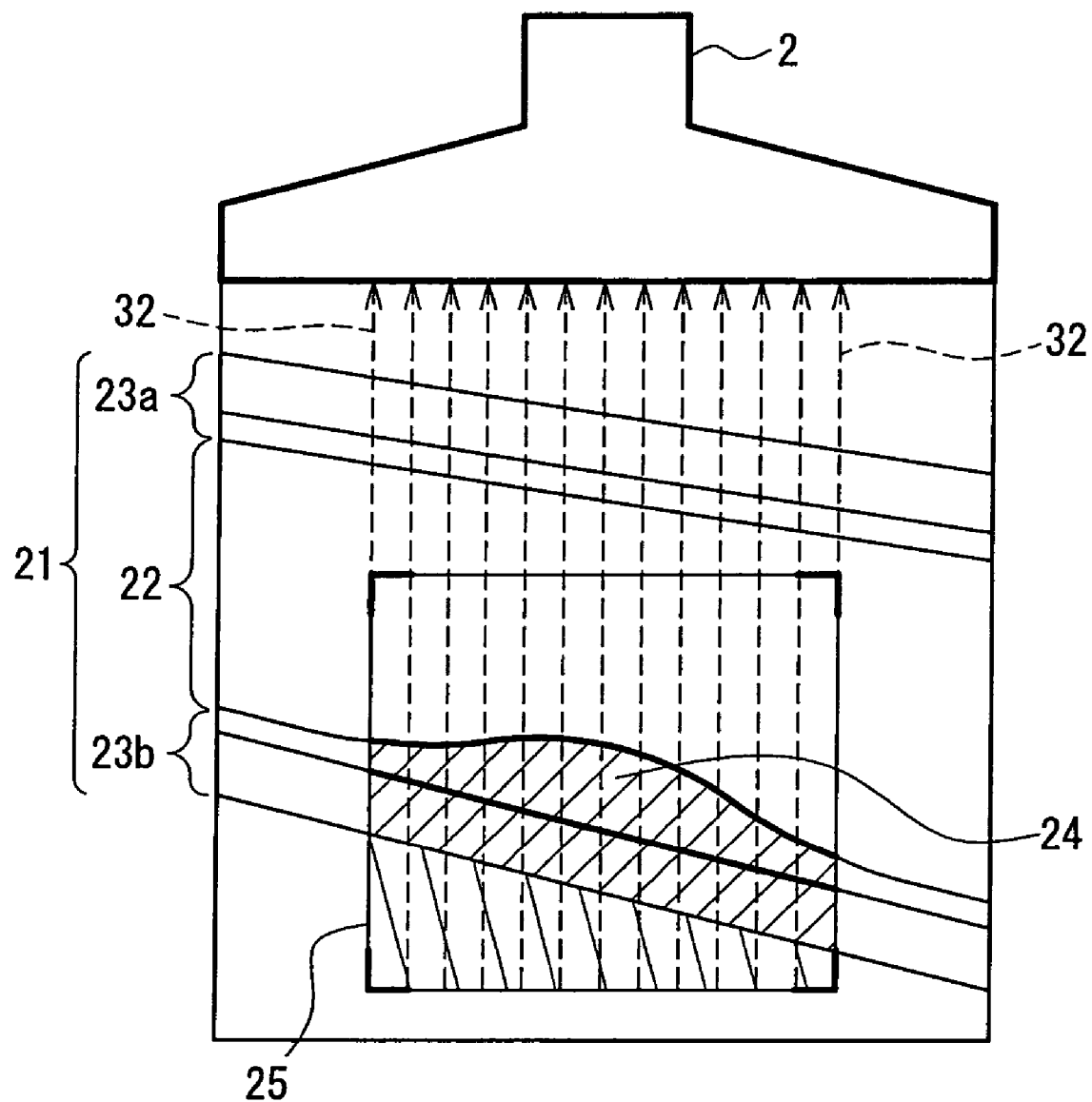
FIG. 5 is a schematic view for explaining another operation of the ultrasonic diagnostic apparatus of FIG. 3.

FIG. 5 is a schematic view for explaining another operation of the ultrasonic diagnostic apparatus according to the present embodiment. As shown in this drawing, a plurality of ultrasonic pulses shown by a plurality of scanning lines 32 may be applied in the longitudinal direction of the blood vessel 21, and a boundary position may be detected along the longitudinal direction of the blood vessel 21 by the boundary position detection unit 7a. With this configuration, an image can be generated that does not include information on the hardness of tissues of blood flow components existing in the RIO 25 that are unnecessary for diagnosis by deleting the information two-dimensionally.

Embodiment 3

An ultrasonic diagnostic apparatus according to Embodiment 3 of the present invention is further provided with the filter processing unit 12 in addition to the configuration of Embodiment 2, as shown in FIG. 3. The filter processing unit 12 performs filter processing of data detected by the boundary position detection unit 7a that shows the boundary position along the longitudinal direction of the blood vessel 21 as follows.

FIGS. 6A to 6C are schematic views for explaining an operation of the ultrasonic diagnostic apparatus according to the present embodiment. Frame (A) and frame (B) in FIG. 6A and FIG. 6B show the boundary detection results within the ROI 25 obtained for each specific cycle such as a heartbeat cycle, which are shown in the order of their detected time.

In the actual site for diagnosis, there is a possibility of the mixing of noise into tracking information on a displacement of the movement of a blood vessel wall, resulting from a plurality of factors such as the movement of the subject and his/her respiratory state, as well as the fixed state of the ultrasonic probe 2. As a result, noise would be mixed in the boundary detection of the blood vessel wall also, like noise 34 in frame (A) or noise 39 in frame (B). In order to minimize the influence of such noise, the filter processing unit 12 performs the filter processing of boundary detection positions concerning mutually neighboring plural positions as in the following expressions (1) and (2). Herein, the boundary detection position at position f is defined as K(f). The position f represents reference numbers of the respective positions indicated in the waveforms of FIGS. 6A to 6C.

$$K(41) = \{K(33) + K(34) + K(35)\}/3 \quad (1)$$

$$K(42) = \{K(38) + K(39) + K(40)\}/3 \quad (2)$$

Further, in order to make a comparison with a result obtained a predetermined number of cycles before, the filter processing according to the following expressions (3) and (4) may be performed, whereby a boundary detection image as in the frame of FIG. 6C can be generated with a minimized influence of noise:

$$K(41) = \{K(34) + K(37)\}/2 \quad (3)$$

$$K(42) = \{K(36) + K(39)\}/2 \quad (4).$$

Herein, for the simplification of description, an example using values at left and right adjacent points are illustrated in the above, which is not a limiting example. For instance, values at left and right two or more points each may be used for the filter processing, from which similar effects can be obtained.

Further, although the above example describes the filter processing using the simple arithmetic mean, weighting for the filter processing may be modified, the arithmetic expressions may be modified, or a plurality of filtering processes may be combined. Moreover, with respect to the movement amounts of the amplitude displacement of the blood vessel wall that is not subjected to the boundary detection, various filtering processes may be applied, followed by the boundary detection.

In this way, even in the case where noise is mixed into tracking information on a displacement of the movement of a blood vessel wall due to a plurality of factors such as the movement of the subject, his/her respiratory state and the fixed state of the ultrasonic probe, a boundary detection image with a minimized influence of noise can be generated.

Embodiment 4

An ultrasonic diagnostic apparatus according to Embodiment 4 of the present invention further is provided with the average processing unit 13 and the stability determination unit 14 in addition to the configuration of Embodiment 2, as shown in FIG. 3. The average processing unit 13 performs average processing of data detected by the boundary position detection unit 7a that shows the boundary position based on data showing a boundary position obtained a predetermined number or more of cycles before. The stability determination unit 14 determines stability of the measurement of detecting the boundary position between the blood vessel wall and the blood flow region based on the data subjected to the average processing by the average processing unit 13.

Figure 7:
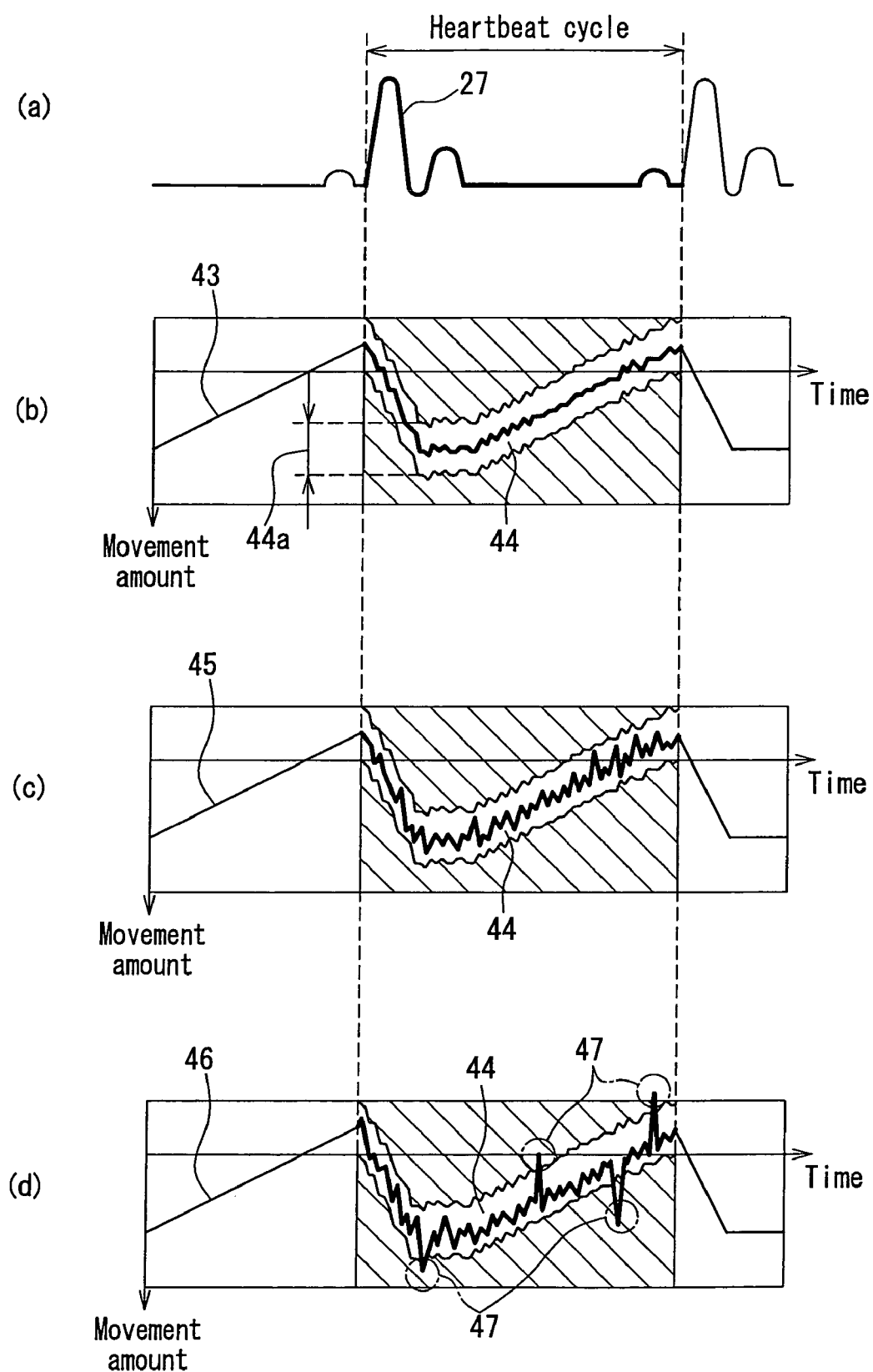
FIG. 7 is a schematic view for explaining an operation of an ultrasonic diagnostic apparatus according to Embodiment 4 of the present invention.

FIG. 7 is a schematic view for explaining an operation of the ultrasonic diagnostic apparatus according to the present embodiment. When ideal measurement data can be obtained in a constant state of the positional relationship between the subject and the ultrasonic probe or in a stable state of the subject by stopping his/her breathing, the blood vessel wall has similar movements (time-varying waveforms of the movement amount of the blood vessel wall) in heartbeats. According to the present invention, the stability of the measurement of detecting the boundary position between the blood vessel wall and the blood flow region is determined by utilizing this.

Waveforms of Portions (b) to (d) in FIG. 7 show the movement tracks of the blood vessel wall in the respective measurement cycles, each in synchronization with the heartbeat cycle of the ECG waveform 27 shown in Portion (a) of FIG. 7. For instance, an allowable range 44 shown in Portion (b) including an allowable error 44a added to a movement track 43 in the immediately preceding cycle is compared with a movement track in a subsequent measurement cycle. In the case where the entire movement track falls within the allowable range 44 as in the movement track 45 of Portion (c), the data is determined as stably measured data. In the case where a deviation 47 outside the allowable range 44 is present as in the movement track 46 shown in Portion (d), it is determined as unstable measurement.

When a measurer is notified of such information indicating stable measurement or unstable measurement in real time, it becomes possible for the measurer to determine during the measurement as to whether the current measurement result is reliable or not. As a result, the measuring time can be shortened.

Naturally, the determination concerning stable measurement or unstable measurement may be made based on a difference between the measurement result in the present cycle and that in the immediately preceding cycle. Further, the determination concerning stable measurement or unstable measurement may be made based on the comparison with not only the immediately preceding cycle but also stably measured movement tracks in a plurality of past cycles.

Further, the threshold value (allowable error 44a) for the determination concerning stable measurement or unstable measurement may be changed. Moreover, regarding the values determined from an echo brightness value that is unsuitable for boundary determination, such as a value of pseudo boundary determination position, a value obtained in the immediately preceding cycle and a value obtained in the present cycle may be compared with each other. By combining these plural functions of determining measuring stability, the reliability of a measurement result can be enhanced further.

In this way, by utilizing a similarity in movement of the blood vessel wall among heartbeats when ideal measurement data is obtained in a constant state of the positional relationship between the subject and the ultrasonic probe or in a stable state of the subject by stopping his/her breathing, the stability of the measurement of detecting the boundary position between the blood vessel wall and the blood flow region can be determined. When a measurer is notified of such information in real time, it becomes possible for the measurer to determine during the measurement as to whether the current measurement result is reliable or not. As a result, the measuring time can be shortened.

Embodiment 5

Figure 8:
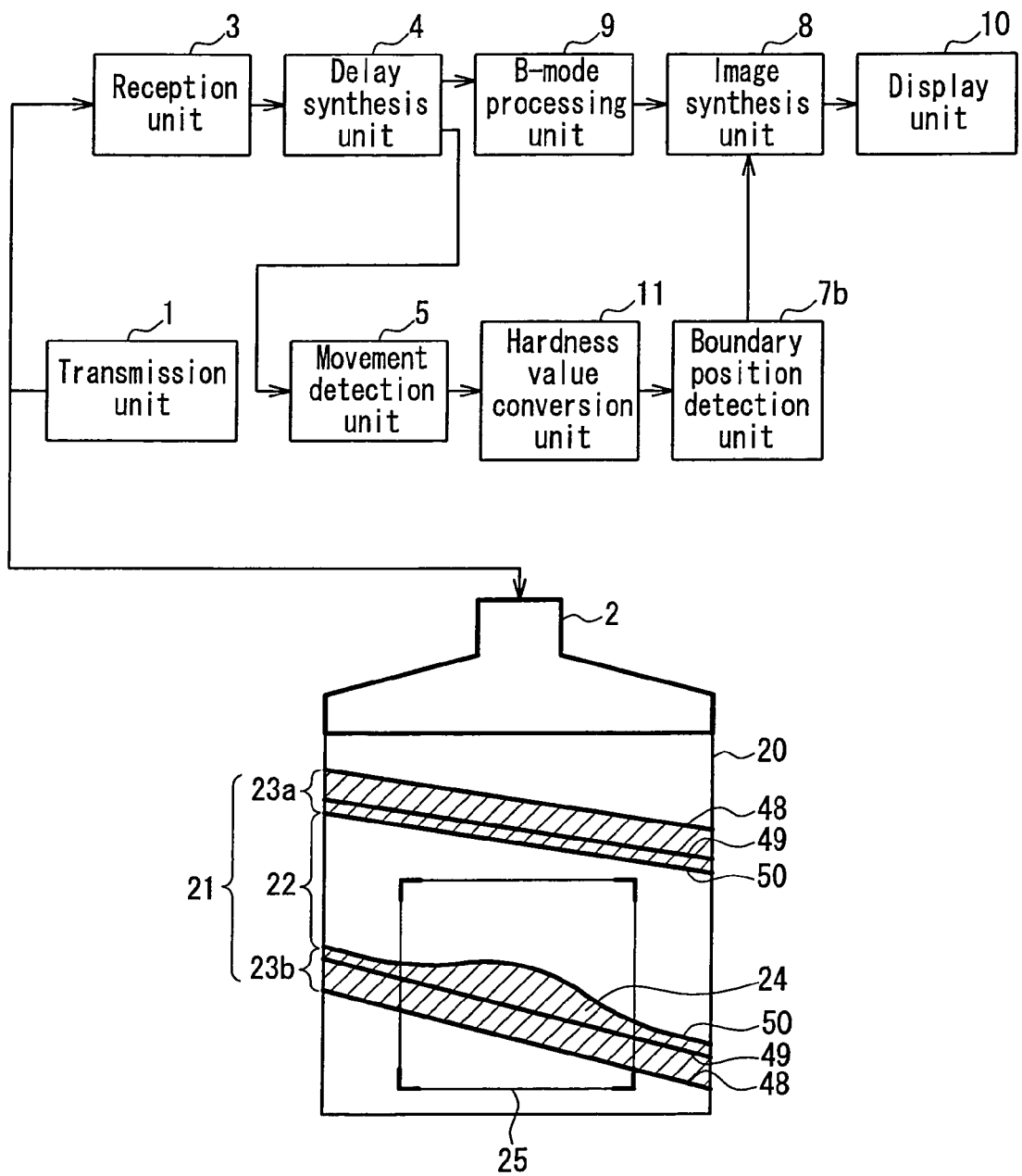
FIG. 8 is a block diagram for explaining a configuration of an ultrasonic diagnostic apparatus according to Embodiment 5 of the present invention.

FIG. 8 is a block diagram schematically showing a configuration of an ultrasonic diagnostic apparatus according to Embodiment 5 of the present invention. The present embodiment enables the measurement of an IMT value of a blood vessel value. The same reference numerals are assigned to elements common to those of the ultrasonic diagnostic apparatus according to the embodiment shown in FIG. 1 or FIG. 3 and duplicate explanations are omitted.

Each of the blood vessel walls shown as an anterior wall 23a and a posterior wall 23b includes an inner membrane 50 that is formed on an inside of the blood vessel wall and faces a blood flow region 22, an outer membrane 48 formed on an outside of the blood vessel wall, and a middle membrane 49 formed between the inner membrane 50 and the outer membrane 48. FIG. 8 shows the state where an atheroma 24 as a local lesion develops between the inner membrane 50 and the middle membrane 49.

A boundary position detection unit 7b according to the present embodiment detects a boundary position between the inner membrane 50 of a blood vessel 21 and a blood flow region 22 and a position of the middle membrane 49 based on hardness values of tissues along the depth direction. The boundary position detection unit 7b further generates a two-dimensionally mapped color display image showing a cross section of the blood vessel 21, and supplies it to an image synthesis unit 8.

The image synthesis unit 8 synthesizes image information supplied from a B-mode processing unit 9 and image information supplied from the boundary position detection unit 7b, and displays the resultant information on a monitor of a display unit 10.

Figure 9:
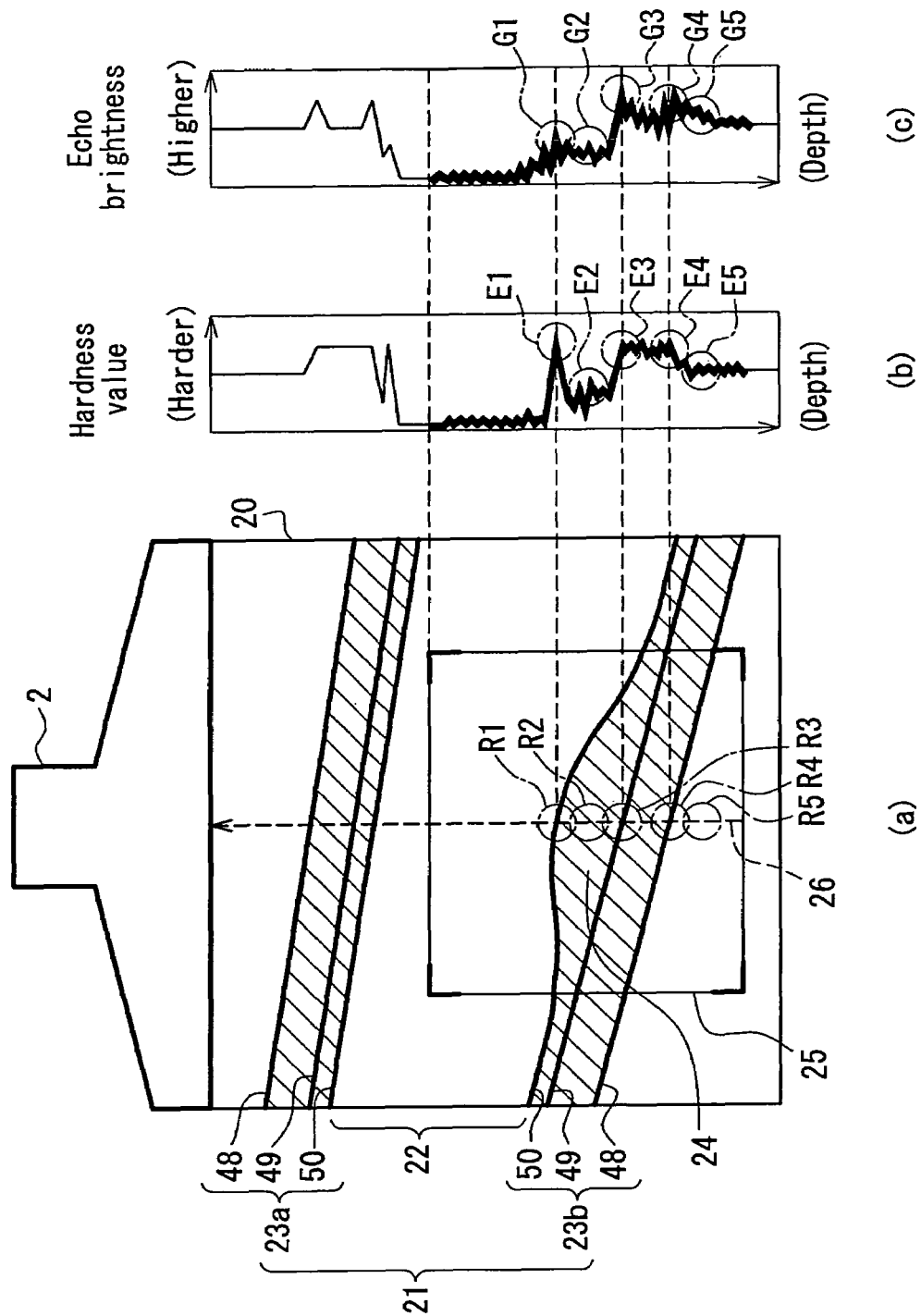
FIG. 9 is a schematic view for explaining an operation of the ultrasonic diagnostic apparatus of FIG. 8.

FIG. 9 is a schematic view for explaining an operation of the ultrasonic diagnostic apparatus according to the present embodiment. Portion (a) of. FIG. 9 shows an image that is the same as the B-mode image 20 shown in FIG. 8. Portion (b) shows a waveform of a variation in hardness value of tissues that is used for detecting a boundary position between the inner membrane 50 and the blood flow region 22. The hardness value is converted by a hardness value conversion unit 11 based on an ultrasonic echo signal obtained by receiving an ultrasonic echo reflected by the blood vessel 21. Portion (c) shows a waveform of a variation in echo brightness in the case where a boundary position is detected using a conventional echo brightness.

Attention is given to point R1, point R2 and point R3 on a scanning line 26 that shows the course of an ultrasonic pulse. Point R1 is placed at a boundary position between the inner membrane 50 and the blood flow region 22. Point R2 is placed in the atheroma 24 on the posterior wall 23b. Point R3 is placed on the middle membrane 49. In order to enable the measurement of an IMT value, assuming that a blood vessel as a target of the measurement has a normal blood vessel wall structure, a maximum peak value and a second peak value of a signal for detecting the boundary in image data should be determined.

As shown by the waveform of Portion (c) that shows a relationship between the conventional echo brightness and the depth from the surface of the skin, a small peak value of the echo brightness can be detected at point G1 corresponding to the boundary position between the posterior wall 23b and the blood flow region 22. However, since a difference from the echo brightness at G2 corresponding to the inside of the atheroma 24 is small, there is a strong possibility that error occurs in the direction toward G3 corresponding to a position on the middle membrane 49. Thus, when the measurement of a blood vessel with an atheroma is attempted, which requires detailed diagnosis, it is impossible to detect the maximum peak value and the second peak value accurately.

In contrast, the use of hardness values of tissues converted by the hardness value conversion unit 11 as in the present embodiment allows point E1 corresponding to point R1 at the boundary position between the posterior wall 23b and the blood flow region 22 to show a much higher peak value than that of point E2 corresponding to R2 disposed in the atheroma 24, which is free from the influence of the echo brightness as shown in the waveform of Portion (b) of FIG. 9. Thus, the maximum peak value at point E1 corresponding to the boundary position between the posterior wall 23b and the blood flow region 22 and the second peak value at point E3 corresponding to R3 indicating the position of the middle membrane 49 can be detected accurately and securely.

As stated above, according to the present embodiment, the boundary position detection unit 7b detects, based on the hardness values of tissues along the depth direction from the surface of the skin, the boundary position between the inner membrane 50 of the blood vessel 21 and the blood flow region 22 and the position of the middle membrane 49 formed between the inner membrane 50 and the outer membrane 48. Therefore, the boundary position between the blood vessel wall and the blood flow region and the position of the middle membrane 49 can be detected correctly without the influence of a variation in brightness value of an inner membrane existing in the subject even in the case where there is a local lesion such as the atheroma 24 in the blood vessel.

Similarly, when attention is given to points E4 and E5 corresponding to points R4 and R5 shown in Portion (a), and points G4 and G5, a position deeper than the second peak where the hardness value decreases can be detected as the position of the outer membrane 48.

Figure 10:
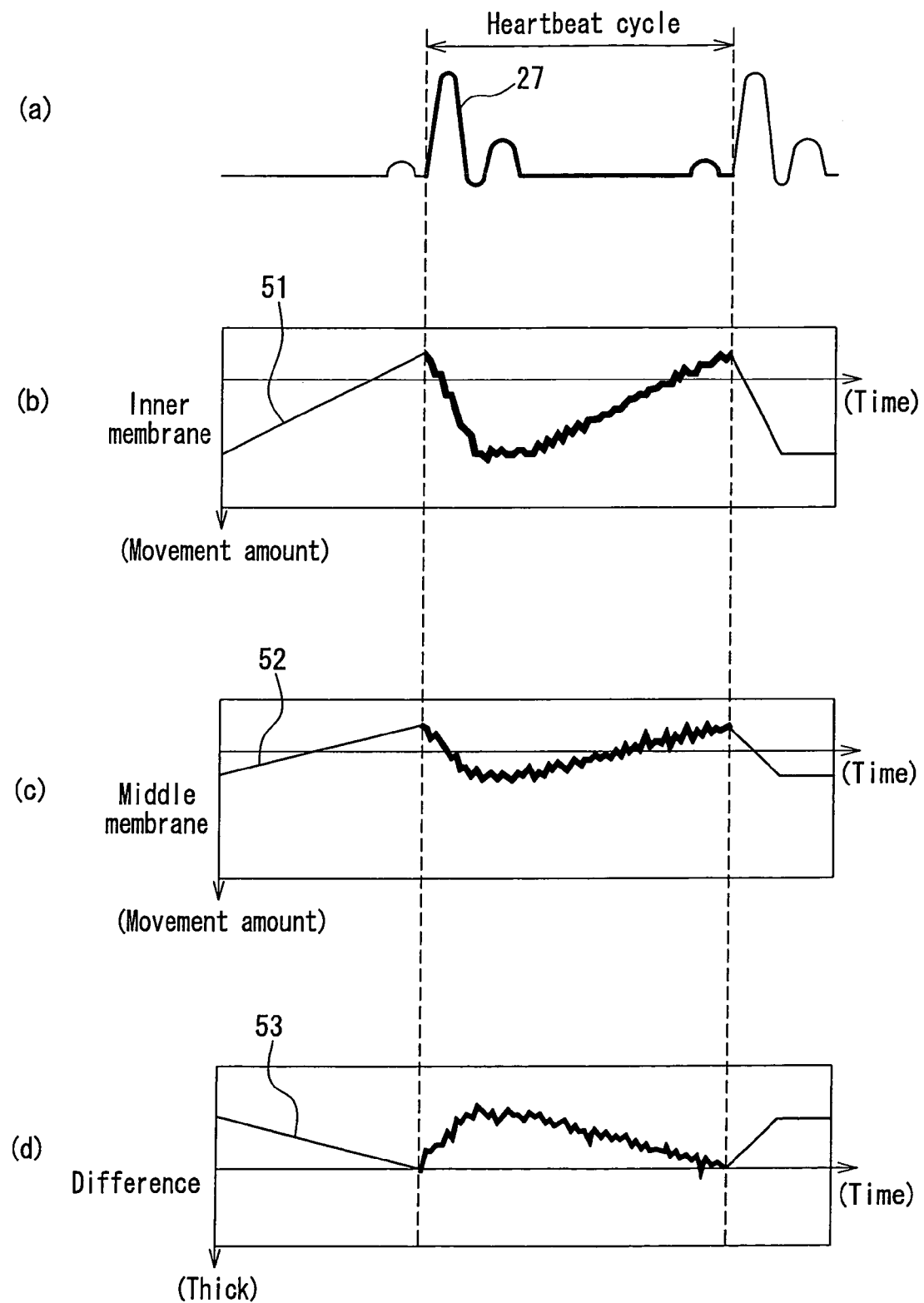
FIG. 10 is a schematic view for explaining an operation of the ultrasonic diagnostic apparatus of FIG. 8.

FIG. 10 is a waveform chart for explaining an operation of the ultrasonic diagnostic apparatus according to the present embodiment. Portion (a) shows a waveform of a heartbeat cycle according to an ECG waveform 27. Portions (b) to (d) show the state of IMT values varying during one heartbeat cycle. For instance, when a track 51 in Portion (b) showing the movement amount of the inner membrane 50 is compared with a track 52 in Portion (c) showing the movement amount of the middle membrane 49, each of the tracks being in synchronization with one heartbeat cycle of the ECG waveform 27, the movement amount shown by the track 52 is smaller than the movement amount shown by the track 51. This is because the hardness values of tissues from the inner membrane 50 to the middle membrane 49 within the range of the IMT value are small, which means that the tissues are soft. Thus, in accordance with a variation in pressure in the blood vessel due to heartbeat, the IMT value decreases as the pressure increases as shown by a track 53 of Portion (d), which is obtained by subtracting the movement amount of the middle membrane 49 shown by the track 52 from the movement amount of the inner membrane 50 shown by the track 51.

For instance, by observing a maximum peak position and a second peak position at a reference time of heartbeat such as a time corresponding to R wave, a variation amount of the IMT value during one heartbeat cycle and a maximum value, a minimum value and an average value of the IMT value also can be confirmed.

Embodiment 6

Figure 11:
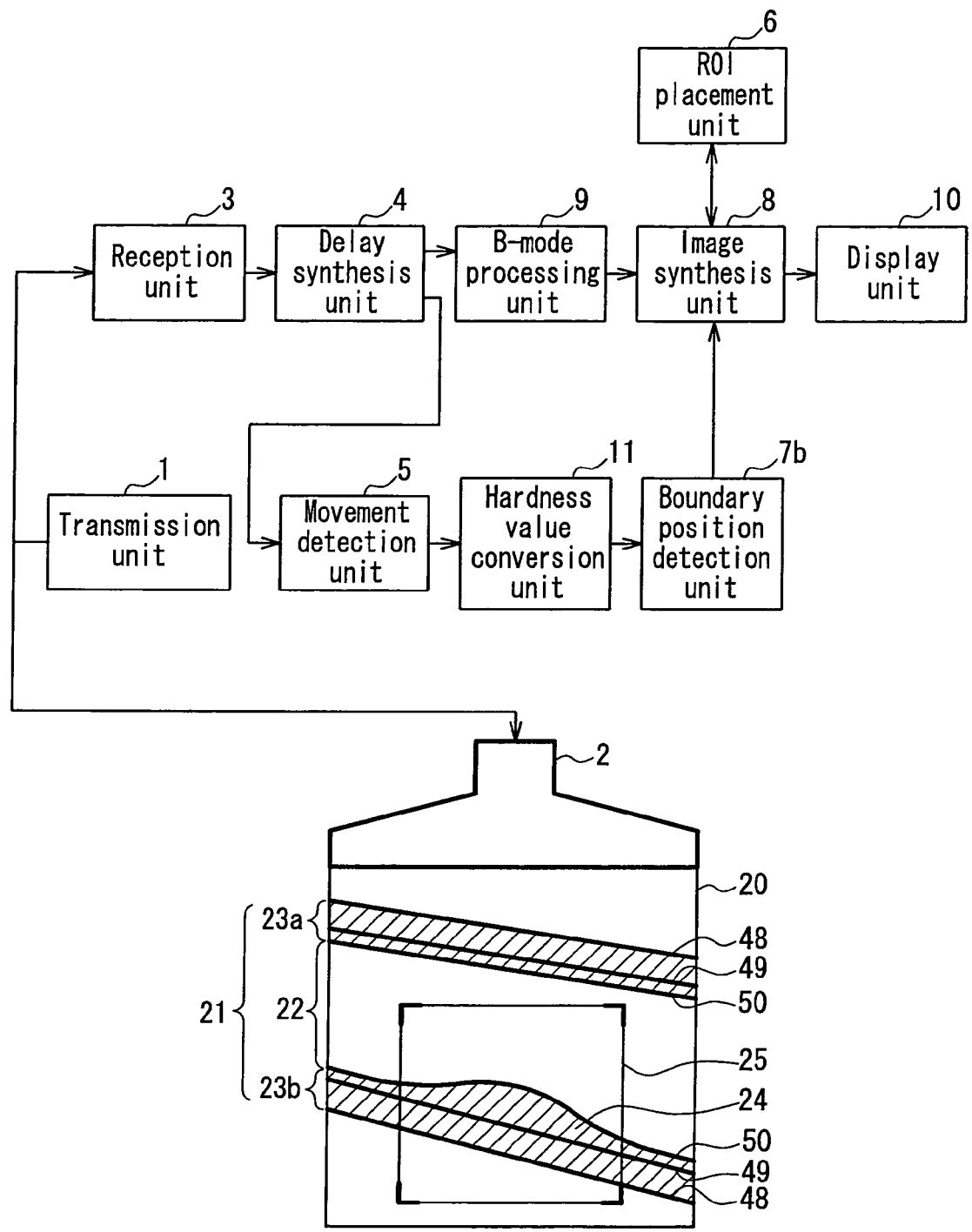
FIG. 11 is a block diagram showing a configuration of an ultrasonic diagnostic apparatus according to Embodiment 6 of the present invention.

FIG. 11 is a block diagram showing a configuration of an ultrasonic diagnostic apparatus according to Embodiment 6. The same reference numerals are assigned to elements common to those of the ultrasonic diagnostic apparatus according to the embodiment shown in FIG. 8 and duplicate explanations are omitted. This ultrasonic diagnostic apparatus is provided with a ROI placement unit 6. The ROI placement unit 6 places a ROI 25, which is for obtaining hardness values of tissues along the depth direction from the surface of the skin, so that the ROI 25 lies over at least one of an anterior wall 23a and a posterior wall 23b. In an example of FIG. 11, the ROI 25 is placed so as to lie over the posterior wall 23b.

An operation of the thus configured ultrasonic diagnostic apparatus will be described below. When the ROI placement unit 6 places a ROI 25 so as to lie over the posterior wall 23b, an ultrasonic pulse is transmitted toward tissues included in the ROI 25, and a boundary position between an inner membrane 50 of a blood vessel 21 and a blood flow region 22 and a position of a middle membrane 49 are detected in a similar manner to the above-described Embodiment 5.

Embodiment 7

Figure 12:
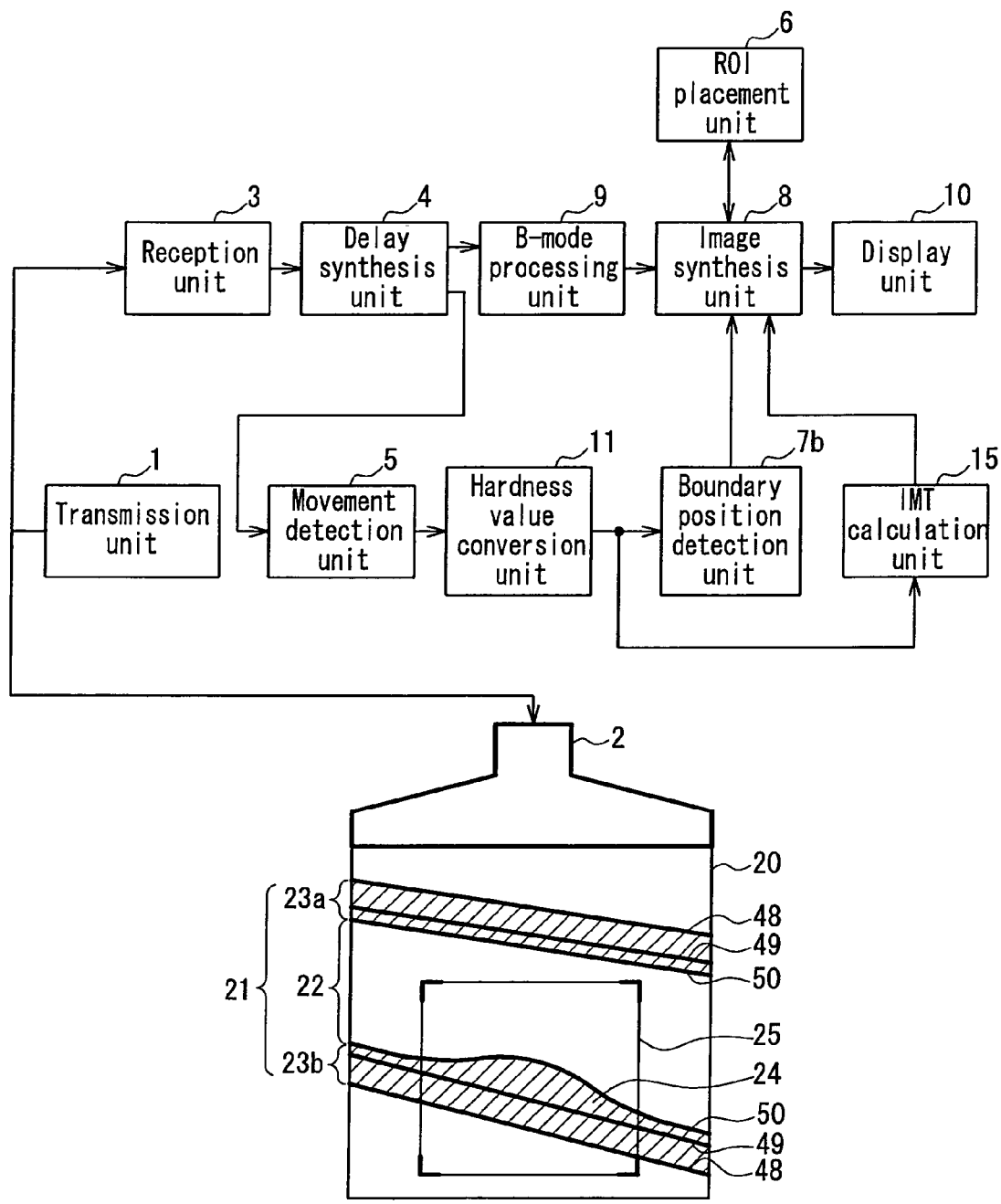
FIG. 12 is a block diagram showing a configuration of an ultrasonic diagnostic apparatus according to Embodiment 7 of the present invention.

FIG. 12 is a block diagram showing a configuration of an ultrasonic diagnostic apparatus according to Embodiment 7. The same reference numerals are assigned to elements common to those of the ultrasonic diagnostic apparatus according to the embodiment shown in FIG. 11 and duplicate explanations are omitted. This ultrasonic diagnostic apparatus is provided with an IMT calculation unit 15. The IMT calculation unit 15 measures a thickness IMT (Intima-Media Thickness) from an inner membrane 50 to a middle membrane 49 based on a variation over time at the boundary position between the inner membrane 50 of the blood vessel 21 and a blood flow region 22 and a variation over time at the position of the middle membrane 49 in one heartbeat cycle. The IMT calculation unit 15 calculates at least one of a maximum value, a minimum value, and an average value of the IMT value in one heartbeat cycle. Thus, a distance between point E1 indicating the maximum peak value and point E3 indicating the second peak value shown in the above-mentioned FIG. 9B can be detected as the IMT value.

Figure 13:
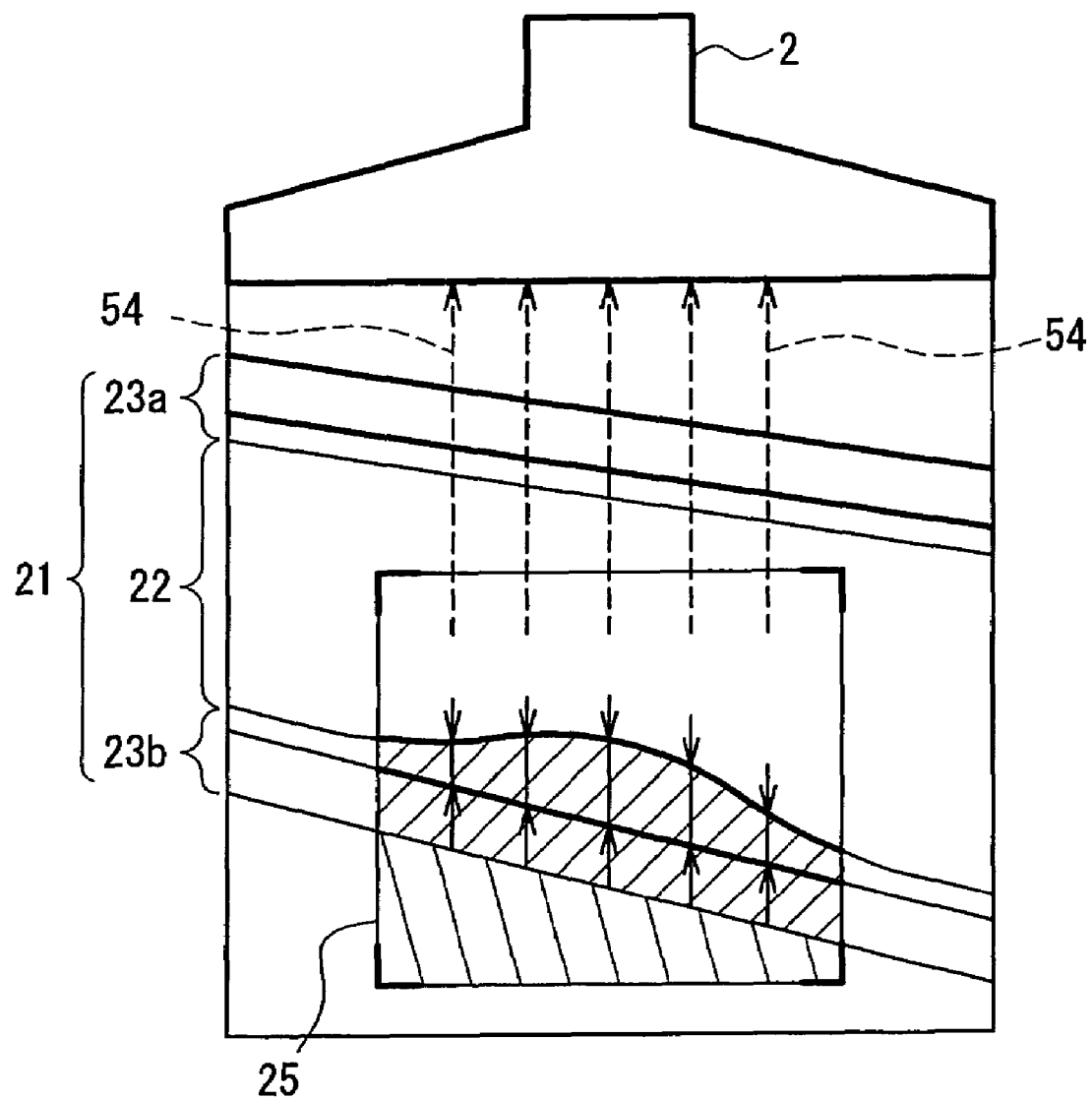
FIG. 13 is a schematic view for explaining an operation of the ultrasonic diagnostic apparatus of FIG. 12.

FIG. 13 is a schematic view for explaining another operation of the ultrasonic diagnostic apparatus according to the present embodiment. As shown in FIG. 13, the ultrasonic diagnostic apparatus can be configured so that a plurality of ultrasonic pulses shown by a plurality of scanning lines 54 are applied along the longitudinal direction of the blood vessel 21, and a boundary position detection unit 7b detects a plurality of IMT values existing in a ROI 25 concurrently along the longitudinal direction of the blood vessel 21. In general, the maximum IMT value often serves as a representative value for the diagnosis, and the position where the maximum IMT value is measured can be displayed on a monitor of a display unit 10.

Embodiment 8

Figure 14:
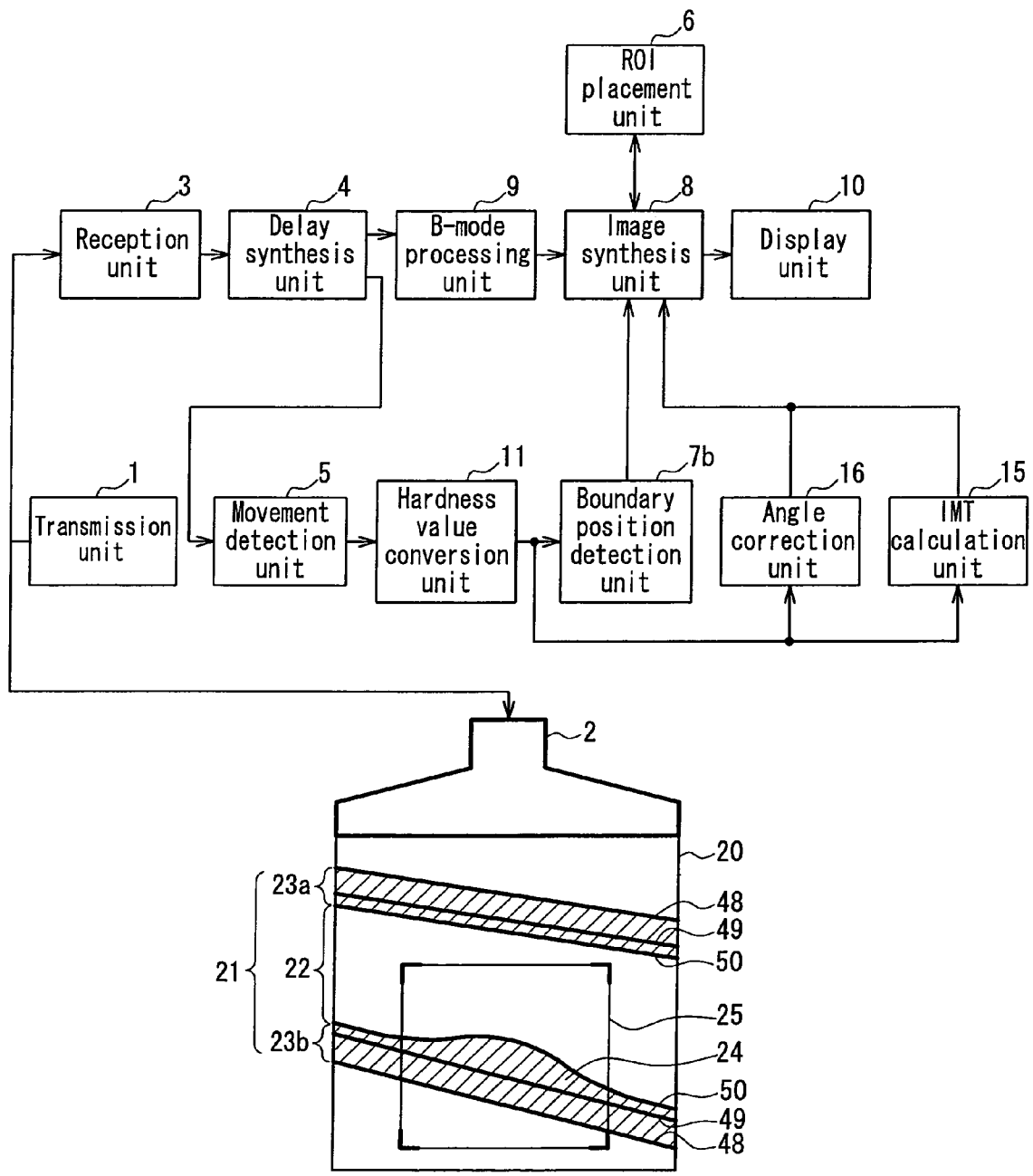
FIG. 14 is a block diagram showing a configuration of an ultrasonic diagnostic apparatus according to Embodiment 8 of the present invention.

FIG. 14 is a block diagram showing a configuration of an ultrasonic diagnostic apparatus according to Embodiment 8. The same reference numerals are assigned to elements common to those of the ultrasonic diagnostic apparatus according to the embodiment shown in FIG. 12 and duplicate explanations are omitted. This ultrasonic diagnostic apparatus is provided with an angle correction unit 16. The angle correction unit 16 performs angle correction with respect to the IMT value calculated by the IMT calculation unit 15 based on a difference in depth from the surface of the skin among a plurality of points.

Figure 15:
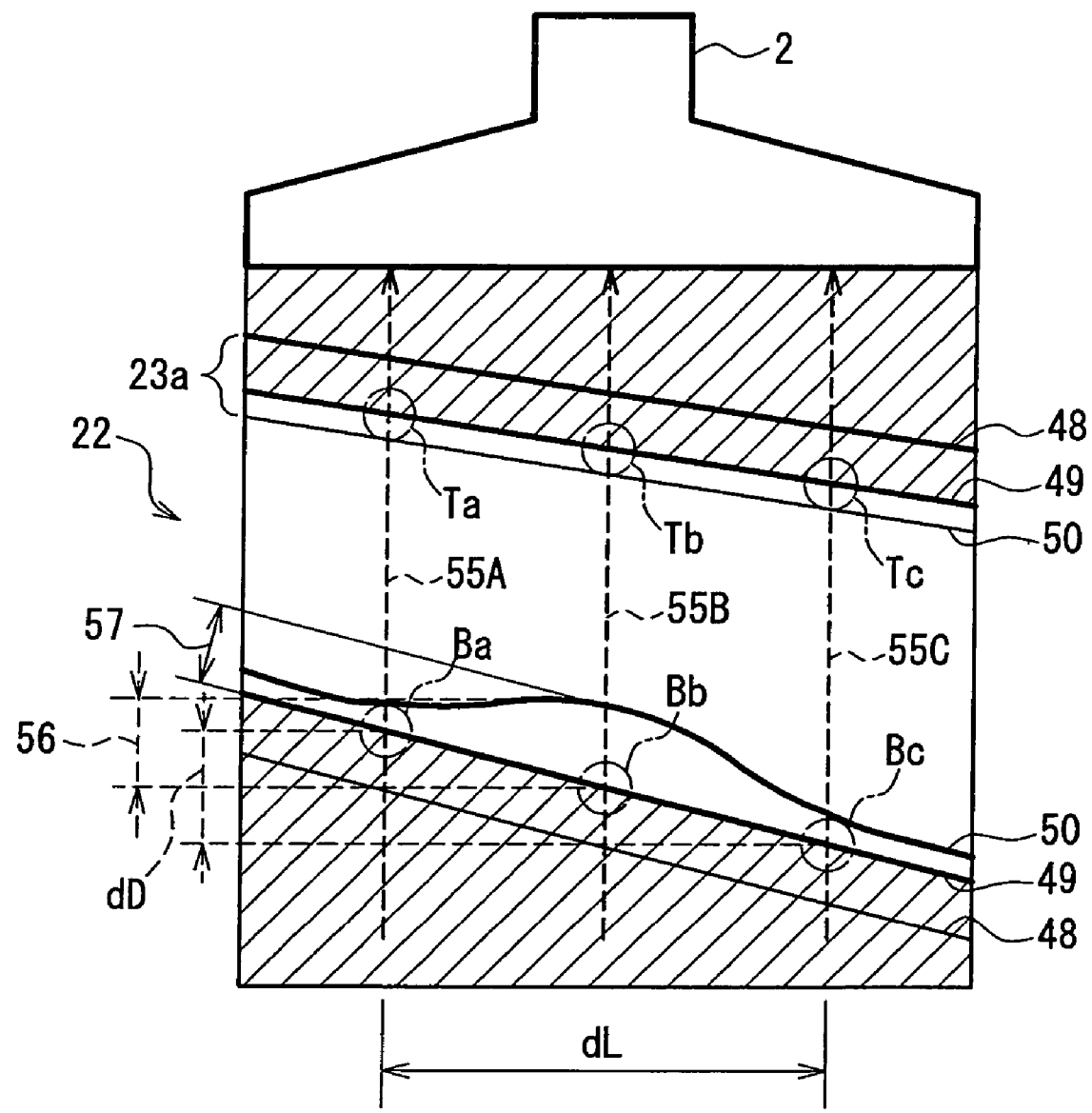
FIG. 15 is a schematic view for explaining an operation of the ultrasonic diagnostic apparatus of FIG. 14.

FIG. 15 is a schematic view for explaining an operation of the ultrasonic diagnostic apparatus according to the present embodiment. An ultrasonic probe 2 applies ultrasonic waves along three scanning lines 55A, 55B and 55C that are spaced along the longitudinal direction of a blood vessel 21. A horizontal distance between the scanning line 55A and the scanning line 55C is denoted with dL. A distance between an intersection point Ba of the scanning line 55A and a middle membrane 49 and an intersection point Bc of the scanning line 55C and the middle membrane 49 is denoted with a difference dD. A distance 56 from the inner membrane 50 to an intersection point Bb of the scanning line 55B and the middle membrane 49 represents an IMT(b) value before the angle correction, and a distance 57 represents an IMT(a) value after the angle correction.

Using positional information of the middle membrane 49 of the blood vessel wall that is obtained based on the plurality of scanning lines 55A, 55B and 55C, angle correction can be performed with respect to an IMT value. For instance, angle correction can be performed with respect to an IMT(b) value 56 at the intersection point Bb using the following expression (5).

$$IMT(a) = IMT(b) \times \sin[\arctan(dL/dD)] \quad (5)$$

Naturally, the accuracy of the angle correction can be enhanced further based on positional information of intersection points Ta, Tb and Tc of a middle membrane 49 on the side closer to the surface of the skin and the scanning lines 55A, 55B and 55C. Alternatively, angle correction may be performed by determining a gradient using the midpoint of the intersection point Ta and the intersection point Ba and the midpoint of the intersection point Tc and the intersection point Bc.

Embodiment 9

Figure 16:
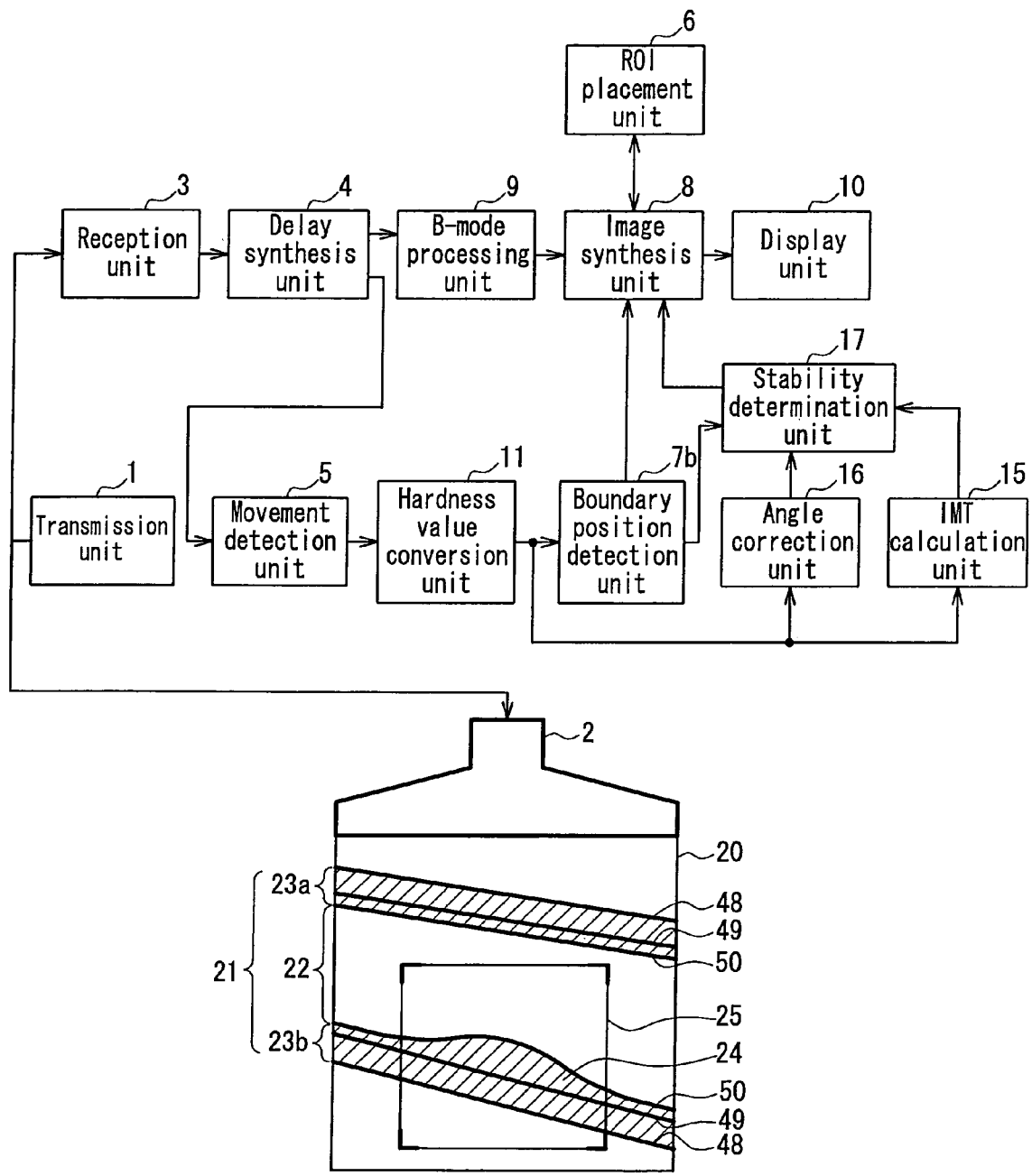
FIG. 16 is a block diagram showing a configuration of an ultrasonic diagnostic apparatus according to Embodiment 9 of the present invention.

FIG. 16 is a block diagram showing a configuration of an ultrasonic diagnostic apparatus according to Embodiment 9. The same reference numerals are assigned to elements common to those of the ultrasonic diagnostic apparatus according to the embodiment shown in FIG. 14 and duplicate explanations are omitted. This ultrasonic diagnostic apparatus is provided with a stability determination unit 17. The stability determination unit 17 determines the stability of an IMT value calculated by the IMT calculation unit 15 by comparing the IMT value calculated by the IMT calculation unit 15 with an IMT value obtained a predetermined number or more of cycles before.

Figure 17:
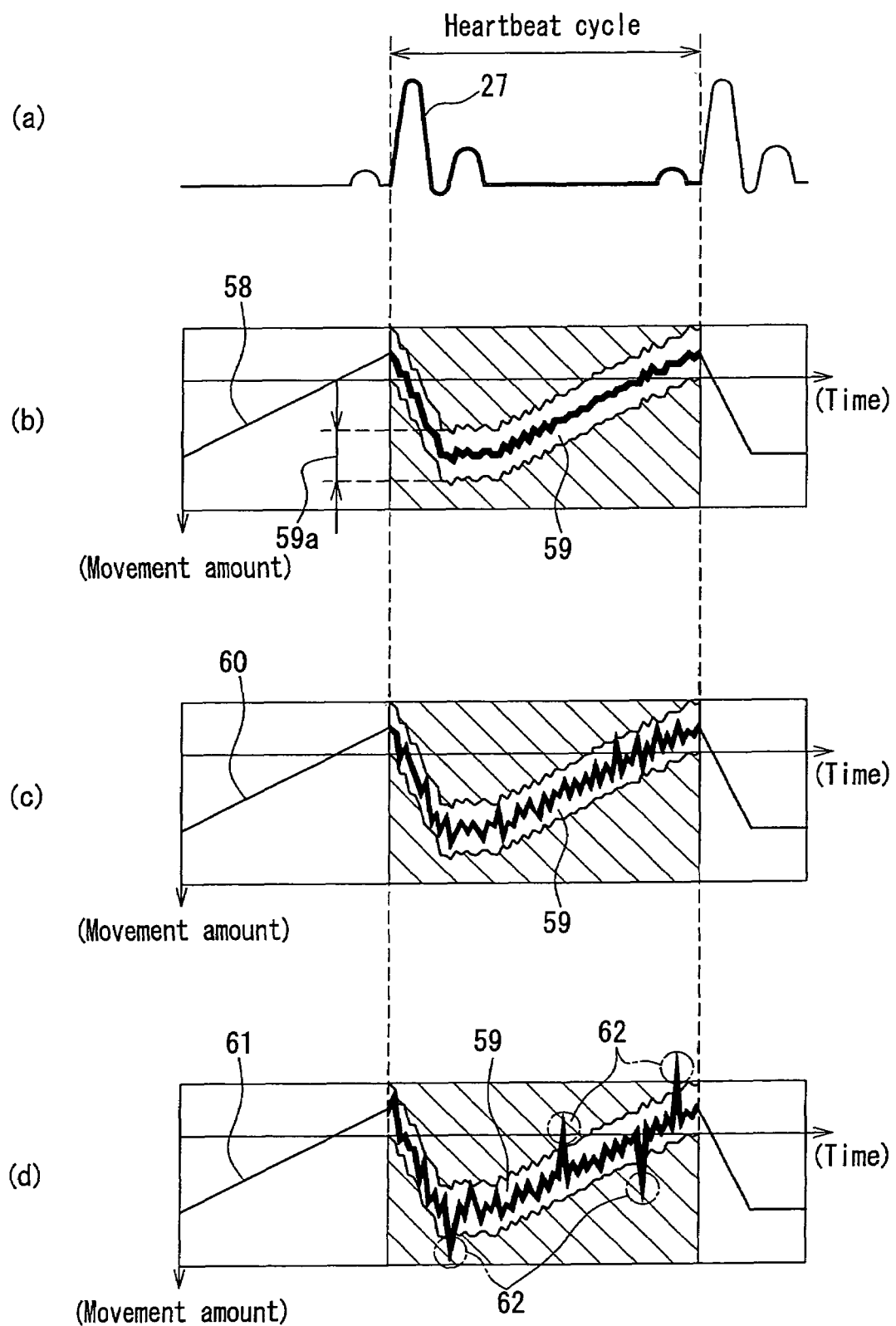
FIG. 17 is a schematic view for explaining an operation of the ultrasonic diagnostic apparatus of FIG. 16.

FIG. 17 is a schematic view for explaining an operation of the ultrasonic diagnostic apparatus according to the present embodiment. When ideal measurement data can be obtained in a constant state of the positional relationship between the subject and the ultrasonic probe or in a stable state of the subject by stopping his/her breathing, the blood vessel wall has similar movements in heartbeats. According to the present invention, the stability of the measurement of detecting an IMT value is determined by utilizing this.

Portions (b) to (d) of FIG. 17 show movement tracks of the blood vessel wall in the respective measurement cycles, each in synchronization with the heartbeat cycle of the ECG waveform 27 shown in Portion (a) of FIG. 17. For instance, an allowable range 59 shown in Portion (b) including an allowable error 59a added to a movement track 58 in the immediately preceding cycle is compared with a movement track in a subsequent measurement cycle. In the case where the entire movement track falls within the allowable range 59 as in the movement track 60 of Portion (c), the data is determined as stably measured data. In the case where a deviation 62 outside the allowable range 59 is present as in the movement track 61 shown in Portion (d), it is determined as unstable measurement.

When a measurer is notified of such information indicating stable measurement or unstable measurement in real time, it becomes possible for the measurer to determine during the measurement as to whether the current measurement result is reliable or not. As a result, the measuring time can be shortened.

Alternatively, the determination concerning stable measurement or unstable measurement may be made based on a difference between the measurement result in the present cycle and that in the immediately preceding cycle. Further, the determination concerning stable measurement or unstable measurement may be made based on the comparison with not only the immediately preceding cycle but also stably measured movement tracks in a plurality of past cycles.

Further, the threshold value (allowable error 59*a*) for the determination concerning stable measurement or unstable measurement may be changed. Moreover, regarding values determined from an echo brightness value that is unsuitable for boundary determination, such as a value of pseudo boundary determination position, a value obtained in the immediately preceding cycle and a value obtained in the present cycle may be compared with each other. By combining these plural functions of determining measuring stability, the reliability of a measurement result can be enhanced further.

INDUSTRIAL APPLICABILITY

According to the present invention, an ultrasonic diagnostic apparatus capable of measuring a state of a blood vessel correctly using ultrasonic waves can be provided. Further, an ultrasonic diagnostic apparatus capable of measuring an IMT value of a blood vessel wall correctly using ultrasonic waves can be provided.

The invention claimed is:

1. An ultrasonic diagnostic apparatus, comprising:
   a transmission unit that transmits at least one ultrasonic pulse, wherein the at least one ultrasonic pulse is transmitted from a skin surface of a subject toward a blood vessel thereof;
   a reception unit that receives an ultrasonic echo signal based on the at least one ultrasonic pulse and converts the same into an electric signal, wherein the ultrasonic echo signal is reflected by the blood vessel to obtain the electric signal of the ultrasonic echo signal representative of a depth direction from the skin surface;
   a movement detection unit that analyzes a phase of the ultrasonic echo signal, wherein the phase of the ultrasonic echo signal is representative of a direction traversing the blood vessel so that the movement detection unit calculates a movement amount in each of a plurality of parts included in a blood vessel wall constituting the blood vessel and a vicinity of the blood vessel wall; and
   a boundary detection unit that detects a boundary position, wherein the detected boundary position is between the blood vessel wall and a blood flow region in a lumen of the blood vessel through which blood flows based on a track indicating a variation in the calculated movement amount for each of the plurality of parts and by detecting a position where neighboring parts have tracks with different features.

2. The ultrasonic diagnostic apparatus according to claim 1, further comprising a ROI placement unit that sets placement of a ROI, wherein the ROI is set where the boundary position along the depth direction from the skin surface is to be detected by the boundary detection unit,
   wherein the ROI placement unit places the ROI so as to lie over at least one of an anterior wall of the blood vessel wall on a side closer to the transmission unit and a posterior wall of the blood vessel wall on a side farther from the transmission unit.

3. The ultrasonic diagnostic apparatus according to claim 1,
   wherein the transmission unit transmits a plurality of ultrasonic pulses toward a plurality of parts along a longitudinal direction of the blood vessel, and the boundary position detection unit detects the boundary position for each of the plurality of parts along the longitudinal direction of the blood vessel.

4. The ultrasonic diagnostic apparatus according to claim 3, further comprising a filter processing unit that performs filter processing, wherein the filter processing unit processes data representing the boundary position along the longitudinal direction of the blood vessel that is detected by the boundary position detection unit.

5. The ultrasonic diagnostic apparatus according to claim 3, further comprising a display unit that displays an image, wherein the image is that of the blood vessel in cross section along the longitudinal direction of the blood vessel based on the boundary position along the longitudinal direction of the blood vessel that is detected by the boundary position detection unit.

6. The ultrasonic diagnostic apparatus according to claim 1, further comprising an average processing unit that performs average processing of data, wherein the data represents the boundary position that is detected by the boundary position detection unit based on data representing a boundary position obtained a predetermined number of measurement cycles before.

7. The ultrasonic diagnostic apparatus according to claim 6, wherein the measurement cycles include a heartbeat cycle of a blood flow that flows through the blood vessel.

8. The ultrasonic diagnostic apparatus according to claim 1, further comprising an average processing unit that performs average processing of data, wherein the data represents the movement amount of the blood vessel wall that is detected by the movement detection unit based on data representing a movement amount obtained a predetermined number of measurement cycles before.

9. An ultrasonic diagnostic apparatus, comprising:
   a transmission unit that transmits at least one ultrasonic pulse, wherein the at least one ultrasonic pulse is transmitted from a skin surface of a subject toward a blood vessel thereof;
   a reception unit that receives an ultrasonic echo signal based on the at least one ultrasonic pulse and converts the same into an electric signal, wherein the ultrasonic echo signal is reflected by the blood vessel to obtain the electric signal of the ultrasonic echo signal representative of a depth direction from the skin surface;
   a movement detection unit that analyzes a phase of the ultrasonic echo signal, wherein the phase of the ultrasonic echo signal is representative of a direction traversing the blood vessel so that the movement detection unit calculates a movement amount in each of a plurality of parts included in a blood vessel wall constituting the blood vessel and a vicinity of the blood vessel wall; and
   a boundary detection unit that detects a boundary position, wherein the boundary position is between an inner membrane of the blood vessel and a blood flow region in a lumen of the blood vessel through which blood flows and a position of a middle membrane of the blood vessel based on a track indicating a variation in the calculated movement amount for each of the plurality of parts and by detecting a position where neighboring parts have tracks with different features.

10. The ultrasonic diagnostic apparatus according to claim 9, further comprising a ROI placement unit that sets placement of a ROI, wherein the ROI is set where the boundary position between the inner membrane of the blood vessel and the blood flow region and the position of the middle membrane are to be detected along the depth direction from the skin surface by the boundary detection unit, wherein the ROI placement unit places the ROI so as to lie over at least one of an anterior wall of the blood vessel wall on a side closer to the transmission unit and a posterior wall of the blood vessel wall on a side farther from the transmission unit.

11. The ultrasonic diagnostic apparatus according to claim 9, further comprising a calculation unit that measures a thickness, wherein the thickness is measured from the inner membrane to the middle membrane based on the boundary position and the position of the middle membrane.

12. The ultrasonic diagnostic apparatus according to claim 11, wherein the calculation unit measures the thickness from the inner membrane to the middle membrane based on a variation over time in the boundary position and a variation over time in the position of the middle membrane in one heartbeat cycle.

13. The ultrasonic diagnostic apparatus according to claim 12, wherein the calculation unit calculates at least one of a maximum value, a minimum value and an average value of the thickness in one heartbeat cycle.

14. The ultrasonic diagnostic apparatus according to claim 11, wherein the transmission unit transmits the plurality of the ultrasonic pulses toward the plurality of parts along the longitudinal direction of the blood vessel, and the calculation unit measures the thickness at each of the plurality of parts.

15. The ultrasonic diagnostic apparatus according to claim 11, further comprising a display unit that displays a part where a maximum thickness is measured among the thicknesses measured at the plurality of parts.

16. The ultrasonic diagnostic apparatus according to claim 9, further comprising an angle correction unit that performs angle correction, wherein the angle correction is performed with respect to a value of the thickness corresponding to an angle formed between a measuring direction of the thickness calculated by the calculation unit and a direction perpendicular to the blood vessel wall.

17. The ultrasonic diagnostic apparatus according to claim 9, further comprising a stability determination unit that determines stability of the thickness calculated by the calculation unit by comparing the thickness calculated by the calculation unit with a thickness obtained a predetermined number of cycles before.

18. The ultrasonic diagnostic apparatus according to claim 9, wherein the transmission unit transmits a plurality of the ultrasonic pulses toward a plurality of parts along a longitudinal direction of the blood vessel, the calculation unit measures the thickness at each of the plurality of parts, and the ultrasonic diagnostic apparatus further comprises a stability determination unit that determines stability of the thickness calculated by the calculation unit by comparing the thicknesses measured at the plurality of parts with each other.

19. The ultrasonic diagnostic apparatus according to claim 11, further comprising a unit that displays a value of the thickness calculated by the calculation unit on a monitor.

20. The ultrasonic diagnostic apparatus according to claim 9, further comprising a unit that displays the boundary position, wherein the unit displays the boundary position and the position of the middle membrane detected by the boundary detection unit on a monitor.

* * * * *